United States Patent
Nguyen et al.

(10) Patent No.: US 12,383,514 B2
(45) Date of Patent: *Aug. 12, 2025

(54) NANO-PARTICLES OF MENAQUINONE AND METHODS OF TREATMENT

(71) Applicant: Epizon, Inc., Woodbridge, CT (US)

(72) Inventors: Sam L. Nguyen, Dana Point, CA (US); John M. Rudey, New York, NY (US)

(73) Assignee: Epizon, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 18/581,968

(22) Filed: Feb. 20, 2024

(65) Prior Publication Data

US 2024/0307321 A1    Sep. 19, 2024

Related U.S. Application Data

(60) Provisional application No. 63/447,305, filed on Feb. 21, 2023.

(51) Int. Cl.
  *A61K 31/122* (2006.01)
  *A61K 9/10* (2006.01)
  *A61K 9/14* (2006.01)
  *A61P 3/14* (2006.01)

(52) U.S. Cl.
  CPC ............. *A61K 31/122* (2013.01); *A61K 9/10* (2013.01); *A61K 9/14* (2013.01); *A61P 3/14* (2018.01)

(58) Field of Classification Search
  None
  See application file for complete search history.

(56) References Cited

U.S. PATENT DOCUMENTS

| 2011/0064803 A1* | 3/2011 | Devane | A61K 9/5026 424/458 |
| 2015/0320702 A1 | 11/2015 | Chou et al. | |
| 2020/0079718 A1* | 3/2020 | Drouet | C07C 69/40 |

FOREIGN PATENT DOCUMENTS

| CN | 106 074 377 A | 11/2016 |
| CN | 110496101 A | 11/2019 |
| WO | 2021206560 A1 | 10/2021 |

OTHER PUBLICATIONS

The International Search Report and Written Opinion, mailed on Jun. 12, 2024, in the related PCT Appl. No. PCT/US24/16473.
Shi Jia et al: "Evaluation of the antitumor effects of vitamin K2(menaquinone-7) nanoemulsions modified with sialic acid-cholesterol conjugate", Drug Delivery and Translational Research, Springer, Germany, vol. 8, No. 1, Aug. 28, 2017, pp. 1-11, XP036414690.
The International Search Report and Written Opinion, mailed on Jun. 8, 2024, in the related PCT Appl. No. PCT/US24/21075.
The US Office Action, mailed on Jul. 24, 2024, in the related U.S. Appl. No. 18/587,915.
The Amendment in response to the US Office Action, submitted on Sep. 17, 2024, in the related U.S. Appl. No. 18/587,915.
Wajih et al., "Successful treatment of calciphylaxis with vitamin K in a patient on haemodialysis," Clinical Kidney Journal, 2022, vol. 15, No. 2, 354-356.
Christiadi et al., "Calciphylaxis in a dialysis patient successfully treated with high-dose vitamin K supplementation," Clinical Kidney Journal, 2018, vol. 11, No. 4, 528-529.

* cited by examiner

*Primary Examiner* — Robert A Wax
*Assistant Examiner* — William Craigo

(57) ABSTRACT

The present application discloses compositions comprising nanoparticles of vitamin K2, and their methods of use.

24 Claims, 9 Drawing Sheets

NANO-PARTICLES OF MENAQUINONE AND METHODS OF TREATMENT

CROSS-REFERENCE TO RELATED APPLICATION

This application claims the priority under 35 USC 119(e) of U.S. Application No. 63/447,305, filed Feb. 21, 2023, entitled "Nano-Particles of Menaquinone and Methods of Treatment", which is incorporated into this application by reference.

FIELD OF INVENTION

The present invention relates to nano-particles of menaquinone, such as MK-7, their compositions and formulations, and for the treatment of diseases associated with vitamin K. The specification further discloses menaquinol, such as menaquinol-4 (MKH2-4) to menaquinol-14 (MKH2-14), their compositions and formulations, and methods for preparation and use for the treatment of diseases associated with vitamin K.

BACKGROUND OF THE INVENTION

Vitamin K is known as a group of structurally similar, fat-soluble vitamins. Vitamin $K_2$ (or vitamin K2) or menaquinone has nine related compounds that can be subdivided into the short-chain menaquinones (such as menaquinone-4 or MK-4) and the long-chain menaquinones, such as MK-7, MK-8, MK-9-14. The vitamins include phylloquinone (K1), menaquinones (K2) and menadione (K3). Plants synthesize vitamin K1 while bacteria can produce a range of vitamin K2 forms, including the conversion of K1 to K2 by bacteria in the small intestines. Vitamin K3 is synthetic version of the vitamin and due to its toxicity, has been banned in by the US Food and Drug Administration for human uses.

It has been established that taking broad-spectrum antibiotics can reduce vitamin K production in the gut by nearly 74% in people compared to those not taking these antibiotics. Diets that are low in vitamin K also decrease the body's vitamin K concentration. Vitamin K1 is preferentially used by the liver as a clotting factor. Vitamin K2 is used preferentially in the brain, vasculature, breasts and kidneys. Vitamin K2 contributes to production of myelin and sphingolipids (fats essential for brain health) and protects against oxidative damage in the brain. Vitamin K2, such as MK-4, promotes bone health by stimulating connective tissue production in bone.

Vitamin K2, which is the main Storage form in animals, has several subtypes, which differ in chain length of the isoprenoid group or residue in the side chains. These vitamin K2 homologues are called menaquinones, and are characterized by the number of isoprenoid residues in their side chains. For example, MK-4 has four isoprene residues in its side chain, and is the most common type of vitamin K2 in animal products. MK-4 is normally synthesized from vitamin $K_1$ in certain animal tissues (arterial walls, pancreas and testes) by replacement of the phytyl group with an unsaturated geranyl group containing four isoprene units. Unlike MK-4, MK-7 is not produced by human tissue. MK-7 may be converted from phylloquinone ($K_1$) in the colon by $E.$ $coli$ bacteria. MK-4 and MK-7 are sold in the U.S. in dietary supplements for bone health. MK-4 has been shown to decrease the incidence of fractures. MK-4, at a dose of 45 ng daily, has been approved by the Ministry of Health in Japan since 1995 for the prevention and treatment of osteoporosis.

It has been established that cardiovascular disease (CVD) is the most frequent cause of death in patients with chronic kidney disease (CKD). When compared to the general population, the cause of death attributed to CVD is about 10-20 times higher in CKD patients when they are being treated with hemodialysis. In addition, it has been demonstrated that vascular calcification and the correlated arterial stiffness is prevalent in the incidence of CVD. Accordingly, the disclosed method of treatment may be applicable for the treatment of peripheral arterial disease. In addition, patient with CKD undergoing dialysis treatment have a 3 times higher risk of bone fractures, such as vertebral fractures and other type of bone fractures.

Vitamin K, including MK-7, are present in low concentrations in a typical diet. It has also been established that there exists a direct correlation between the level of vitamin K in a patient's blood and the incidence of vascular calcification, bone density and bone strength. Accordingly, the supplemental use of vitamin K, such as MK-7 and its also fat-soluble hydroquinone (menaquinol) as nanoparticle formulations, as disclosed herein, may provide significant clinical benefit for reducing vascular calcification noted, in part, by arterial stiffness, and increase bone mineralization or increase in bone mineral density, that will help treat or prevent CVD, and treat or prevent bone diseases in patients with CKD. In one aspect, the disclosed method for the administration of MK-7, as nanoparticle compositions or formulations, as disclosed herein, may be used in the treatment or reduction of vascular calcification, increase in bone mineral density and for the treatment, reduction or prevention of bone diseases, such as in patients with CKD.

It has also been established that in food products, vitamin K1 is bound to the chloroplast membrane of leafy green vegetables. MK-4, which is derived from the conversion of menadione, a synthetic analog of vitamin K, is found in animal products such as eggs and meats. Long chain menaquinones such as MK-7, MK-8 and MK-9, are found in fermented foods such as cheese, curd and sauerkraut. It has also been established that the effects of long chain MK-n such as MK-7 on normal blood coagulation is greater and longer lasting than vitamin K1 and MK-4. MK-7 has also been shown to have a long half-life in serum when compared to MK-4, providing a better carboxylation-grade of osteocalcin compared to Vitamin K1. See Sato et al., *Nutrition Journal,* 2012, 11:93.

Nutritional doses of MK-7 can be established to be well absorbed in humans, and as a consequence, provide a significant increase in the serum for MK-7 levels.

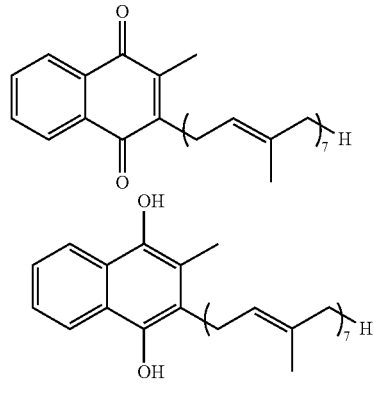

MK-7

Menaquinol-7

It has been determined that over one third of the drugs listed in the U.S. Pharmacopoeia are insoluble or poorly soluble in water. In addition, over 40% of drugs are insoluble in the human body, which is significant considering that there are over 5,000 small molecules under development. Solubility and stability issues are two of the challenging properties that hinder drug development. In addition, aqueous solubility is necessary for formulating many organic compounds that are being developed as pharmaceuticals. Traditional formulation systems for highly insoluble drugs have involved the application of a combination of organic solvents, surfactants and emulsion, among other methods. Poorly water-soluble drugs, such as vitamin K2 or MK-7, for example, are typically eliminated from the gastrointestinal tract before being able to be absorbed into the circulation. It is known that the rate of dissolution of a particular compound or drug can increase with increasing surface area; or with decreasing particle size. Accordingly, there has a been significant focus in the development of the nanoparticles for the delivery of insoluble drugs, drugs with low solubility or poorly soluble drugs. Nanoparticles are generally considered to be solid particles with a diameter of about 1 nm and 1000 nm.

The foregoing examples of the related art and limitations are intended to be illustrative and not exclusive. Other limitations of the related art will become apparent to those of skill in the art upon a reading of the specification and a study of the drawings or figures as provided herein.

SUMMARY OF THE INVENTION

A continuing need exists for novel formulations that are effective for these indications. The following embodiments, aspects and variations thereof are exemplary and illustrative are not intended to be limiting in scope.

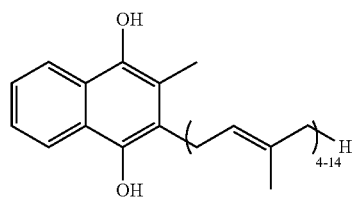

Menaquinol-4 to Menaquinol-14

In one aspect, there is provided a composition comprising nanoparticles (or nano-sized particles) of water soluble vitamin K2, wherein the nanoparticles have an average particle size of about 0.1 nm to 1,000 nm. In one aspect, the vitamin K2 is selected from the group consisting of MK-4 (menaquinone-4), MK-5 (menaquinone-5), MK-6 (menaquinone-6), MK-7 (menaquinone-7), MK-8 (menaquinone-8), MK-10 (menaquinone-10), MK-11 (menaquinone-11), MK-12 (menaquinone-12), MK-13 (menaquinone-13) and MK-14 (menaquinone-14). In another aspect, the vitamin K2 is MK-7. In another aspect, the vitamin K2 compound, that includes MK-4 to MK-14 and also MKH2-4 to MKH2-14, is selected from the group consisting of MKH2-4 (menaquinol-4), MKH2-5 (menaquinol-5), MKH2-6 (menaquinol-6), MKH2-7 (menaquinol-7), MKH2-8 (menaquinol-8), MKH2-9 (menaquinol-9), MKH2-10 (menaquinol-10), MKH2-11 (menaquinol-11), MKH2-12 (menaquinol-12), MKH2-13 (menaquinol-13) and MKH2-14 (menaquinol-14), where the compound is stabilized for storage and administration. In another aspect, the nanoparticles have an average particle size of less than 200 nm, 175 nm, 150 nm, 125 nm, 115 nm, 100 nm, 90 nm, 80 nm or less than 75 nm. In another aspect, the composition is a stable composition when stored at room temperature.

In one variation, the nanoparticles have an average particle size range of about 10 nm to 750 nm, 20 nm to 700 nm, 40 nm to 600 nm, 50 nm to 500 nm, 60 nm to 400 nm; or about 45 nm to 95 nm. In another variation, the nanoparticles have an average particle size of about 70 nm to 300 nm, 80 nm to 200 nm, 90 nm to 175 nm, 100 nm to 150 nm or about 120 to 130 nm. In another variation, the nanoparticles have an average particle size of about 75 nm to 175 nm, 85 nm to 165 nm, 95 nm to 155 nm, 105 nm to 145 nm, 145 nm to 175 nm or about 155 nm to 165 nm. In another variation, the nanoparticles have an average particle size range of about 75 nm to 105 nm, 85 nm to 90 nm. In another variation, the average particle size may be about 155 nm.

In another aspect of the above composition, the nanoparticles are prepared using a homogenizer selected from the group consisting of a rotor stator homogenizer, a bead mill homogenizer or a mortar and pestle homogenizer. In one variation, the nanoparticles are prepared using a milling process, such as wet milling, wet milling using a high-pressure homogenizer, a dry milling process or jet milling. See T. Niwa et al., Universal wet-milling technique to prepare oral nanosuspension focused on discovery and preclinical animal studies—Development of particle design method, International Journal of Pharmaceutics, Vol. 405, 1-2, 28 Feb. 2011, 218-227; T. Niwa et al., Design of Dry Nanosuspension with Highly spontaneous Dispersible Characteristics to Develop Solubilized Formulation for Poorly water-Soluble Drugs, Pharmaceutical Research, 28, 2339-2349, 2011.

In another aspect, the composition further comprises at least one emulsifier (or solubilizer) selected from the group consisting of Poloxamer 188, Polysorbate 80, Polysorbate 20, Vit E-TPGS (TPGS), TPGS-1000, TPGS-750-M, Solutol HS 15, PEG-40 Hydrogenated castor oil, Kolliphor RH 40, PEG-35 Castor oil, PEG-8-glyceryl caprylate/caprate, PEG-32-glyceryl laurate, PEG-32-glyceryl palmitostearate, Polysorbate 85, polyglyceryl-6-dioleate, sorbitan monooleate, Capmul MCM, Maisine 35-1, glyceryl monooleate, glyceryl monolinoleate, PEG-6-glyceryl oleate, PEG-6-glyceryl linoleate, oleic acid, linoleic acid, propylene glycol monocaprylate, propylene glycol monolaurate, polyglyceryl-3 dioleate, polyglyceryl-3 diisostearate, carboxymethylcellulose (CMC), polysorbate 80 (P80) and lecithin; or mixtures thereof. In another aspect, the emulsifier is selected from Polysorbate 80, Vit E-TPGS, Solutol HS 15, PEG-40 Hydrogenated castor oil and PEG-35 Castor oil.

In one aspect, the composition further comprises at least one bioavailability enhancer selected from the group consisting of medium chain fatty acids, omega-3 fatty acids, capric acid, caprylic acid, alkylglycosides, chitosan, trimethylated chitosan, ethylene glycol tetraacetic acid, ethylene diamine tetraacetic acid, salicylic acid, genistein (5,7-dihydroxy-3-(4-hydroxyphenyl)chromen-4-one)), and their pharmaceutically acceptable salts.

In another aspect, the composition is a nanosuspension in water, or nano-particle emulsion in water. In yet another aspect, the composition, the nanosuspension or nano-particle emulsion is at least 5-times more soluble than commercially available (via chemical synthesis or fermentation) non-homogenized vitamin K2, or vitamin K-2 that are not formed or prepared as nanoparticles, such as MK-7. In one variation, the composition is at least 2-times, 3-times, 5-times, 7-times, 10-times, 15-times, 20-times or more soluble than commercially available, non-homogenized vitamin K2. As used herein, the "non-homogenized" vitamin K2 is a commercially available vitamin K2, such as MK-7, MK-8, MK-9, etc. . . . , that has not been homogenized, milled or otherwise prepared as nanoparticles or a nanosuspension, as described herein. In another aspect, the vitamin K2 is MK-7. In another aspect, the nanosuspension of vitamin K2 is prepared or performed at a concentration of 0.01 mg/mL in water. In yet another aspect, the nanosuspension is in a water solution in a Fed State Simulated Intestinal Fluid (FeSSIF). In yet another aspect, the solubility is determined after 10 minutes in a FeSSIF.

In another aspect, the composition further comprises a pharmaceutically acceptable excipient, wherein the composition is effective for the treatment of a condition associated with vitamin K, or for the treatment of osteoporosis or arteriosclerosis.

In another embodiment, there is provided a method for the treatment of a disease in a mammal selected from the group consisting of neurodegenerative diseases, retinopathy, rheumatoid polyarthritis, atherosclerosis, amyotrophic lateral sclerosis, cerebral ischemia, cataracts, systemic infections, pathologies associated with cutaneous aging and with senescence in tissues, pathologies associated with mitochondrial dysfunction, cachexia associated with under nutrition, wherein the treatment is associated with the increase in the longevity of mammals, the method comprises the administration of a therapeutically effective amount of any of the composition as described above.

In another embodiment, there is provided a method for treating a mammal with a disease selected from the group consisting of vitamin K deficiency, osteoporosis, a proliferative disease, and a cardiovascular disease, comprising administering to the mammal a therapeutically effective amount of any of the composition as described above. In yet another embodiment, there is provided a method for the treatment or prevention of osteoporosis and/or osteopenia, the method comprising administering to a patient in need of treatment, a therapeutically effective amount of a composition as described above. In yet another embodiment, there is provided a method of treating, preventing, slowing the progression of, arresting, and/or reversing calciphylaxis in a mammal in need thereof, the method comprising administering to the mammal a therapeutically effective amount of any of the above described composition, and a pharmaceutically acceptable excipient, to prevent, slow the progression of, arrest, or reverse calciphylaxis. In one aspect, the mammal has distal calciphylaxis and/or central calciphylaxis. In another aspect, the mammal has diabetes, chronic kidney disease or end stage renal disease.

In one variation of the above method, the mammal has stage 3, stage 4 or stage 5 chronic kidney disease. In another variation of the method, the mammal is undergoing hemodialysis. In another variation of the method, the mammal is receiving non-warfarin-based anti-coagulant therapy. In another variation of the method, the anti-coagulant therapy is oral anti-coagulation therapy. In yet another variation of the method, the anti-coagulation therapy comprises an inhibitor of Factor Xa activity selected from apixaban, rivaroxaban, betrixaban, edoxaban, otamixaban, letaxaban, eribaxaban or fondaparinux; or Factor IIa activity selected from dabigratran or argatroban.

Treatment of COPD:

Chronic Obstructive Pulmonary Disease (COPD) is a term used to describe progressive lung disease that makes breathing difficult. The two primary forms of COPD are emphysema and chronic bronchitis. In addition, elastinolysis (proteolysis of elastin) is a key feature of COPD. It contributes to the loss of arterial flexibility and promotes calcification of the intimal media of blood vessels. It also has been shown to be a strong predictor of mortality in COPD patients (Rabinovich et al., (2016) *Circulating desmosine levels do not predict emphysema progression but are associated with cardiovascular risk and mortality in COPD*, ERJ Express doi: 10.1183/13993003.01824-2015). MGP has been demonstrated to inhibit the production of matrix metalloproteases that promote elastinolysis. Vitamin D may be a critical determinant of the rate of elastin degradation, and that low Vitamin D levels lead to low MGP activity that is inadequate to protect from elastinolysis (Piscaer et al., (2017) *Vitamin D deficiency: the linking pin between COPD and cardiovascular diseases*?RESP. RES. 18:189). Without wishing to be bound by the theory, enhanced production of activated (carboxylated) MGP by administration of vitamin K2, as disclosed herein, can act to suppress the deleterious effects of elastinolysis in a subject having COPD thereby to prevent, or slow the progression of, or reverse the one or more symptoms of COPD. In addition, the treatment of the degradation of elastin may be effective for the treatment of Covid, such as Covid-19 and variants thereof. Accordingly, the nanoparticle formulations as disclosed herein may be administered for the treatment or the prevention of the degradation of elastin, and diseases associated with the degradation of elastin.

In one aspect of any of the above method, the mammal has chronic obstructive pulmonary disease (COPD). In another aspect of the method, the mammal has a calciphylaxis-related dermal lesion. In one variation of the method, the administration of the composition reduces the total surface area of the dermal lesion by at least 10%, 20%, 30%, 40%, 50%, 60%, 70%, 80%, 90% or 100%. In another variation of the method, the administration of the above composition to the mammal increases the mammal's serum T50 value by at least 10%, 20%, 30%, 40%, 50%, 60%, 70%, 80%, 90% or 100%, relative to the mammal's serum T50 value prior to administration of the above composition. In another variation of the method, administration of the composition increases a ratio of a carboxylated to a non-carboxylated of a Vitamin K dependent protein in plasma of the mammal after administration of the composition is greater than prior to administration of the composition.

In one embodiment, there is provided a method of treating, preventing, slowing the progression of, arresting and/or reversing tissue calcification or calciphylaxis in a mammal (or subject), the method comprising administering to the mammal at least 0.1 mg of the above described composition per day, to prevent, slow the progression of, and/or arrest tissue calcification, including soft tissue calcification, wherein the above described composition is administered in a pharmaceutical composition. In another embodiment, there is provided a method of treating, preventing, slowing the progression of, arresting and/or reversing tissue calcification in a pre-diabetic mammal (or subject) with diabetes, chronic kidney disease or a combination thereof, and in need thereof, the method comprising administering to the mammal at least 0.01 mg or at least 0.1 mg of the composition of any one of the above described composition per day, to prevent, slow the progression of, and/or arrest tissue calcification, wherein the above described composition is administered in a pharmaceutical composition. In one variation of the method, the mammal has diabetes. In another variation, the mammal has type II diabetes. In another variation, the mammal has been diagnosed as pre-diabetic. In one aspect, the mammal has chronic kidney disease. In one variation of the above method, the mammal has stage 4 or 5 chronic kidney disease/end stage renal disease. In another variation of the method, the mammal is undergoing hemodialysis. In another variation, the mammal is receiving non-warfarin based anti-coagulant therapy. In another variation, the anti-coagulant therapy is oral anti-coagulation therapy. In another variation, the anti-coagulation therapy comprises an inhibitor of Factor Xa activity selected from apixaban, rivaroxaban, betrixaban, edoxaban, otamixaban, letaxaban, eribaxaban or fondaparinux; or Factor IIa activity selected from dabigratran or argatroban.

In another variation, there is provided a method of treating, preventing, slowing the progression of, arresting, and/or reversing tissue calcification in a mammal undergoing hemodialysis, and in need thereof, the method comprising administering to the mammal at least 0.01 mg or at least 0.1 mg of the composition per day, thereby to prevent, slow the progression, arrest, and/or reverse tissue calcification, wherein the composition is administered in a pharmaceutical formulation. In one variation of the method, the mammal has diabetes. In another aspect, the present application discloses a fortified food or drink formulation comprising adding to the food or drink a composition comprising a composition of any one of those disclosed herein.

In another aspect of the method, the proliferative disease is selected from the group consisting of cancer, leukemia and an inflammatory disease. In another embodiment, there is provided a method for treating a mammal with a disease selected from the group consisting of vitamin K deficiency, osteoporosis, a proliferative disease, and a cardiovascular disease, comprising administering to the mammal a therapeutically effective amount of any of the above composition. In one aspect, the cancer is selected from the group consisting of melanoma, lung cancer, breast cancer, leukemia, neuroblastoma, glioblastoma, cervical, colorectal, pancreatic, bladder, renal, prostate, ovarian and head and neck.

In another embodiment, there is provided a method for treating, preventing, slowing the progression of, arresting and/or reversing Alzheimer's disease (AD) in a mammal or a subject in need thereof, the method comprising administering to the mammal or subject at least 0.1 mg of the composition of any one of the above composition per day, to prevent, slow the progression of, and/or arrest or reverse Alzheimer's disease.

In another aspect, the application discloses a pharmaceutical composition comprising a therapeutically effective amount of a menaquinone as disclosed above, and a pharmaceutically acceptable excipient, wherein the composition is effective for the treatment of a condition associated with vitamin K selected from for the treatment of osteoporosis and arteriosclerosis.

In another aspect of the above method, the anti-coagulant therapy is oral anti-coagulation therapy. In another aspect, the anti-coagulation therapy comprises an inhibitor of Factor Xa activity selected from apixaban, rivaroxaban, betrixaban, edoxaban, otamixaban, letaxaban, eribaxaban or fondaparinux; or Factor IIa activity selected from dabigratran or argatroban. In another aspect, the mammal has chronic obstructive pulmonary disease (COPD). In another aspect, the mammal has a calciphylaxis-related dermal lesion. In another aspect of the method, administration of the composition reduces the total surface area of the dermal lesion by at least 10%, 20%, 30%, 40%, 50%, 60%, 70%, 80%, 90% or 100%. In another aspect of the method, administration of the composition as disclosed herein, to the mammal increases the mammal's serum T50 value by at least 10%, 20%, 30%, 40%, 50%, 60%, 70%, 80%, 90% or 100%) relative to the mammal's serum T50 value prior to administration of the disclosed compositions. In another aspect, administration of the disclosed composition increases a ratio of a carboxylated to a non-carboxylated of a Vitamin K dependent protein in plasma of the mammal after administration of the composition is greater than prior to administration of the composition. In one aspect of the method, the increase of the ratio of a carboxylated to a non-carboxylated of a Vitamin K dependent protein in plasma of the mammal after administration of the composition is by at least 5%, 10%, 15%, 20%, 25%, 30%, 35%, 40%, 45% 50%, 55%, 60%, 65%, 70%, 75%, 80%, 85%, 90%, 95%, or 100% relative to the ratio prior to administration.

In certain embodiments of the above, the administration of the disclosed composition decreases the amount of a non-carboxylated Vitamin K-dependent protein in the subject's plasma, for example, by at least 5%, 10%, 15%, 20%, 25%, 30%, 35%, 40%, 45% 50%, 55%, 60%, 65%, 70%, 75%, 80%, 85%, 90%, 95% or 100% relative to the amount prior to administration of the compositions. In certain variations, the Vitamin K-dependent protein is selected from Matrix Gla Protein (MGP), Growth Arrest Specific Gene 6 (Gas-6) protein, PIVKA-II protein, osteocalcin, activated Protein C, activated Protein S, factor II, factor VII, factor IX, and factor X.

In certain variation of the above methods, the administration of the composition increases the plasma level of osteoprotegerin or Fetuin A, for example, by at least 5%, 1, 1%, 20%, 25%, 30%, 35%, 40%, 45% 50%, 55%, 60%, 65%, 70%, 75%, 80%, 85%, 90%, 95%, or 100% relative to the plasma concentration of osteoprotegerin or Fetuin A prior to administration of the compositions. In other variations, the administration of the composition decreases the plasma level of D-Dimer or Highly Sensitive C Reactive Peptide (hs-CRP), for example, by at least 5%, 10%, 15%, 20%, 25%, 30%, 35%, 40%, 45% 50%, 55%, 60%, 65%, 70%, 75%, 80%, 85%, 90%, 95% or 100% relative to the plasma concentration of D-Dimer or Highly Sensitive C Reactive Peptide (hs-CRP) prior to administration of the compositions.

In certain variations of the above methods, the method may include administering from about 0.1 mg to about 200 mg of the composition to the subject per day. In other variations, the method may include administering from about 0.1 mg to about 150 mg of the composition to the subject per day. In other variations, the method may include administering from about 0.1 mg to about 100 mg of the composition to the subject per day. In other variations, the method may include administering from about 2 mg to about 200 mg of the composition to the subject per day. In certain variations, the method can include administering from about 2 mg to about 250 mg of the composition to the subject per day. In other variations, the method may include administering from about 2 mg to about 250 mg of the composition to the subject per day. In other variations, the method may include administering from about 2 mg to about 100 mg of the composition to the subject per day. In other variations, the method may include administering from about 3 mg to about 100 mg of the composition to the subject per day. In other variations, the method may include administering from about 0.5 mg to about 75 mg of the composition to the subject per day, for example, administering 0.1 mg, 1 mg, 2 mg, 3 mg or 10 mg of the composition to the subject per day.

In certain variations, the composition is administered to the subject for at least 2 weeks, 4 weeks, 6 weeks, 8 weeks, 3 months, 6 months, 1 year, or indefinitely as needed. If the subject is undergoing hemodialysis, the composition may be administered to the subject for a period that includes at least the duration of hemodialysis.

In another variation of the method for treatment of calciphylaxis, in addition to measuring the change/reduction in lesion size following administration of the disclosed compositions, pre and post drug dosing administration, a biopsy may be taken of the relevant lesions using von Kassa Staining to determine tissue levels of PTH and evidence of change in calcium and phosphate deposition in dermal arterioles.

As disclosed herein, the presence of a uremic oxidative blockade is determined by measuring increased plasma lipid peroxidation, e.g., by detection of increased F2 isoprostanes (Morrow et al. (1990) *A series of prostaglandin F2-like compounds are produced in vivo by humans by a non-cyclooxygenase, free radical-catalyzed mechanism*, PROC. NATL. ACAD. SCI. USA 87:9383-9387), increased isolevuglandin-plasma protein adducts (Salomon et al. (2000) *Isolevuglandin-protein adducts in humans: Products of free radical induced lipid oxidation through the isoprostane pathway*, BIOCHIM BIOPIHYS ACTA 1485:225-235), increased breath ethane (Handelman et al. (2000) J AM. SOC. NEPHROL. 11:271A); increased protein and amino acid oxidation, e.g., by detection of tyrosine residue oxidation (Heinecke et al. (1999) *Detecting oxidative modification of biomolecules with isotope dilution mass spectrometry: Sensitive and quantitative assays for oxidized amino acids in proteins and tissues*, METHODS ENZYMOL. 300:124-144), cysteine or methionine residue oxidation, lysine oxidation and threonine oxidation, thiol oxidation and carbonyl formation in plasma proteins (Himmelfarb et al. (2000) *Plasma protein thiol oxidation and carbonyl formation in chronic renal failure*, KIDNEY INT. 58:2571-2578); reactive aldehyde formation, e.g., by detecting glyoxal, methylglyoxal, acrolein, glycoaldehyde, and parahydroxy phenacetaldehyde (Miyata et al. (1999) *Alterations in nonenzymatic biochemistry in uremia: Origin and significance of 'carbonyl stress' in long-term uremic complications*. KIDNEY INT. 55:389-399); increased reactive carbonyl compounds, e.g., by measuring hydrazine formation after reaction with 2,4-dinitrophenylhydrazine; diminished plasma glutathione levels and glutathione peroxidase function (Ceballos-Picot et al. (1996) *Glutathione antioxidant system as a marker of oxidative stress in chronic renalfailure*, FREE RADIC. BIOL. MED. 21:845-853); and increased ratio of oxidized to reduced thiols (Hultberg et al. (1995) *Reduced, free, and, total fractions of homocysteine and other thiol compounds in plasma from patients with renal failure*, NEPHRON 70:62-67; Himmelfarb et al. (2002) *Plasma aminothiol oxidation in chronic renal failure*, KIDNEY INT 61:705-716; Ward et al. *Polymorphonuclear leukocyte oxidative burst is enhanced inpatients with chronic renal insufficiency*, J AM. SOC. NEPHROL. 5:1697-1702).

In another embodiment, there is provided a method of treating, preventing, slowing the progression of, arresting and/or reversing tissue calcification in a pre-diabetic mammal (or subject) with diabetes, chronic kidney disease or a combination thereof, and in need thereof, the method comprising administering to the mammal at least 0.01 mg of the disclosed composition, to prevent, slow the progression of, and/or arrest tissue calcification, wherein the composition is administered in a pharmaceutical composition. In another aspect of the method, the mammal has diabetes. In yet another aspect, the mammal has type II diabetes; or the mammal has been diagnosed as pre-diabetic. In another aspect, the mammal has chronic kidney disease. In another aspect of the above method, the mammal has stage 4 or 5 chronic kidney disease/end stage renal disease. In yet another aspect, the mammal is undergoing hemodialysis. In another aspect, the mammal is receiving non-warfarin based anti-coagulant therapy. In another aspect, the anti-coagulant therapy is oral anti-coagulation therapy. In another aspect of the method, the anti-coagulation therapy comprises an inhibitor of Factor Xa activity selected from apixaban, rivaroxaban, betrixaban, edoxaban, otamixaban, letaxaban, eribaxaban or fondaparinux; or Factor IIa activity selected from dabigratran or argatroban.

In another embodiment, there is provided a method of treating, preventing, slowing the progression of, arresting, and/or reversing tissue calcification in a mammal undergoing hemodialysis, and in need thereof, the method comprising administering to the mammal at least 0.01 mg or 0.1 mg of substantially pure composition as disclosed herein per day, thereby to prevent, slow the progression, arrest, and/or reverse tissue calcification, wherein the disclosed composition is administered in a pharmaceutical composition. In another aspect, the mammal has diabetes.

Vitamin K Metabolism: Development of vascular and soft tissue calcification following the failure to regenerate reduced forms of vitamin K: Vitamin K is an essential enzymatic co-factor that is required for posttranslational modifications of vitamin K dependent (VKD) proteins. While there are numerous VKD proteins many are clinically relevant to ESRD patients. They include central coagulation factors such as factors II VII IX and X as well as intercellular matrix proteins including Matrix GLA-1 and Osteocalcin. Under normal conditions, vitamin K is reduced to vitamin K hydroquinone (KH2) by the enzyme NADPH oxidase. It is only the reduced form of vitamin K that is able to function as a co-factor for gamma glutamate carboxylase (GGCX) which catalyzes the carboxylation of vitamin K dependent proteins. Warfarin blocks the generation of vitamin K hydroquinone by acting as a reductive sink. The enzymatic carboxylation of glutamate residues results in further oxidation of vitamin KH2 to 2-3 epoxide vitamin K (FIG. 2). The final step of the vitamin k cycle requires the enzymatic oxidation of vitamin K 2-3 epoxide back to its native structure. This step is catalyzed by vitamin K oxidative reductase (VKOR) and is a component of the vitamin K cycle that is also blocked by the oxidative effects of Warfarin. The observation that Warfarin blocks both the generation of vitamin K hydroxyquinone (KH2) as well as the regeneration of Vitamin K2 2-3 epoxide helps to explains why the incidence of calciphylaxis and other forms of dystrophic calcification is higher among patients receiving Warfarin therapy.

In one variation, the supplementation of the disclosed compositions reduces the risk for vascular and soft tissue calcification by increasing the formation of primary calciprotein particles (CPP) composed of Fetuin A and Carboxylated Matrix GLA-1 Proteins. Under normal physiologic conditions plasma calcium and phosphate concentrations are near supersaturation and thus would be expected to precipitate in blood vessels and soft tissue as crystalline hydroxyapatite. The observation that this process does not occur suggests the presence of potent chemical and biologic means for blocking pathologic calcification. Recent studies have shown that circulating calcium phosphate crystals are complexed with two calcification inhibiting proteins to form primary calciprotein particles (CPPs). These protein-mineral complexes are composed of primarily of Fetuin A; a liver derived protein that has been shown to prevent vascular calcification. A second protein in lower quantities is Matrix Gla-1 protein that also functions to prevent pathologic calcification. Matrix Gla-1 is a vitamin K dependent protein and early work have shown that formation of the Fetuin-Matrix Gla-1 mineral nanoparticles (primary calciproteins CPP) is dependent upon the gamma carboxylation of Matrix Gla-1. Pre-clinical studies suggest that the calciprotein system functions as an alternative means for preventing pathologic calcification when humoral lines of defense such as pyrophosphate, magnesium and albumin are overwhelmed. The "absorption" of calcium-phosphate crystals by primary CCPs occurs in a coordinated and time-dependent process.

The time to 50% saturation ($T_{50}$) of primary CCPs is an accurate and highly sensitive means for determining the capacity of plasma to "sink" or "absorb" excess calcium phosphate crystals. Patients with a short $T_{50}$ times suggests a reduced capacity to absorb calcium phosphate crystals whereas patients with prolonged $T_{50}$ times are consistent with high capacities. Recent clinical studies have validated the $T_{50}$ test and confirmed that low $T_{50}$ times are associated with increased myocardial infarctions, heart failure and all-cause mortality. Thus, any clinical intervention that can increases the synthesis of circulating primary CCPs will improve the capacity to prevent pathologic calcification. It is noted that because patients with CKD and ESRD exhibits reduced levels of carboxylated Matrix Gla-1 protein and that this process is essential for the formation of primary CPP. Accordingly, supplementation or administration of the disclosed compositions and compositions in CKD or ESRD patients will reduce the risk for pathologic calcification and prevent the development of vascular and soft tissue calcification.

Supplementation or administration of the disclosed compositions may prevent or slow the development of soft tissue and vascular calcification in dermal tissues by restoring production of Carboxylated Matrix Gla-1 and GAS-6.

The regeneration of Vitamin K involves two key enzymes: vitamin K 2-3 epoxide oxidative reductase (VKOR) and NAD(P)H: quinone oxidoreductase (NQO1). As shown in the figure, VKOR reduces 2-3 Vitamin K epoxide to vitamin K quinone while NADPH reduces Vitamin K quinone to its hydroxyquinone form (KH2). Recent studies have shown that VKOR has two distinct isoforms exist (VKORC-1 and VKORC1-Like-1 [VKORC1-L1]) that differ in both enzymatic properties and tissue distribution. For example, Westhofen et. al has shown that compared to VKORC1, VKOCR-L1 has a 3-fold lower affinity for 2-3 epoxide vitamin K Subsequent work supported the hypothesis that VKOR-L1 is a specialized isoform that protects against oxidant injury through the regeneration of vitamin K. When cultured HEK 293T cells were incubated with $H_2O_2$, VKOR-L1 expression was increased and evidence of membrane oxidant injury was reduced. The clinical observation that calciphylaxis and vitamin K-dependent vascular calcification are more common in the dermis raises the question of whether there is differential expression of VKOR enzymes in the skin. To address this question, Casper et. al determined mRNA expression of key enzymes involved in regeneration of vitamin K. As shown in FIGS. 3 and 4, skin exhibited the lowest level of VKOR-C1 than any other tissue. Moreover, expression of NADPH in the dermis was below the level of detection. These observations suggest that any condition or procedure (i.e., hemodialysis) that blocks re-constitution of vitamin K predisposes that tissue to pathologic calcification.

The oxidative properties of uremic plasma as well as the oxidative effects of dialysis itself results in a "metabolic block" and an accumulation of 2-3 epoxide vitamin K and a reduction in the intracellular levels of vitamin K2. The "down-stream" effects of this blockade include the inability to gamma carboxylate key proteins involved in preventing soft tissue and vascular calcification. The oxidative effects of hemodialysis exacerbate this effect which may explain in part the predilection of ESRD patients to develop calciphylaxis and vascular calcification.

The relationship between vitamin K and circulating vitamin K dependent proteins in CKD-ESRD Patients: It is widely recognized that despite dietary deficiencies, vitamin K levels among ESRD patients may not be reduced. For example, Holder et al. studied 172 stable dialysis patients and found that only 6% of patients exhibited a clinically significant deficiency in vitamin K. However, when patients were examined for the level of carboxylated osteocalcin, a full 60% of patients has reduced levels. To confirm that was a general effect of reduced vitamin K activity, the authors also measured PIVKA-II; another vitamin K dependent protein. Indeed, a full 90% of both CKD and ESRD patients were found to have reduced levels of carboxylated prothrombin. In a similar study, Pilkey et al. measured the vitamin K1 levels in 142 ESRD patients and found that the majority of patients had adequate vitamin K stores but 93% of patients had uncarboxylated osteocalcin levels that were greater than 20% of total levels. It is noted that there was no correlation between total vitamin K1 and the levels of circulating of uncarboxylated osteocalcin. This unexpected finding is consistent with the hypothesis that in uremic patients, total vitamin K levels can be normal while generation of reduced forms are blocked by the oxidative properties of uremia.

In one variation, the supplementation or administration of the disclosed composition will reverse hemodialysis induced inhibition of vitamin K dependent proteins through normalization of functional reduced forms of vitamin K. The observation that oxidant conditions can disrupt the vitamin K cycle suggests that the oxidant load generated during hemodialysis could contribute to the high rates of vascular and soft tissue calcification observed within the ESRD population. Work by Himmelfarb et. al and others have confirmed that the simple delivery of hemodialysis can lead to the oxidation of numerous tissue proteins. For example, hydroxyl amino acid side chains be oxidized to oxidized to carbonyl groups. In a study of CKD and ESRD patients, Himmelfarb et al. demonstrated using carbonyl side chain oxidation as a measure of global oxidant burden, Himmelfarb et al. demonstrated that both CKD and ESRD patients exhibit a higher percentage (15-fold) (See FIG. 5) of carbonyl proteins compared to normal controls. The percentage of carbonyl proteins was even higher among patients receiving dialysis demonstrating that not only does dialysis reduce oxidant burden, it appears to contribute to it. As shown in FIG. 5, patients with uremia were found to have up to 15-fold higher levels of carbonylated proteins. Accordingly, the oxidative load generated by the delivery of hemodialysis leads to oxidation of the function vitamin K hydroquinone (KH2) to the non-functional native vitamin. The oxidation of KH2 by hemodialysis block its ability to function as a co-factor for GGCX which down-stream leads to reduced gamma carboxylation of vitamin K dependent proteins.

To confirm that uremia and hemodialysis disrupts the vitamin K cycle, the ratio of vitamin K quinone to 2-3 epoxide vitamin K and vitamin K hydroxyquinone (KH2) may be determined in patients with normal renal function, CKD (Stage IV & V) and ESRD patients. To determine whether the very process of hemodialysis further disrupts the vitamin K cycle, we can measure the levels of oxidized vitamin K in immediately prior to hemodialysis, then at mid-dialysis (2 hrs) and 30 minutes post dialysis. Previous studies examining the interactions between Warfarin and vitamin K metabolism have shown that 2-3 Epoxide Vitamin K are readily measured. Compared to controls, patients with CKD and ESRD will have higher levels of 2-3 epoxide vitamin K and lower levels of vitamin hydroquinone (KH2). To determine whether a loss of reduced forms of Vitamin K (KH2) leads to a reduction in the carboxylation of vitamin K dependent proteins, we can measure the levels of the following biomarkers in control, CKD (Stage IV and V) and ESRD (Pre-Post hemodialysis). Matrix GLA-1 protein; Growth Arrest Specific Gene 6 (Gas-6) proteins; PIVAK-II protein; Osteocalcin; Protein C; Protein S; Fetuin A; and Osteoprotegerin (Dialysis Plasma Levels: 6.7±2.2 pmole/L). We extend these studies by including patients receiving stable 3×/week hemodialysis. The levels of carboxylated and uncarboxylated vitamin K dependent proteins in pre-dialysis serum may be compared levels obtained at hour 2 and the end of a dialysis session. The oxidative effects of dialysis itself will lead to a reduction in the level of carboxylated Vitamin K dependent proteins.

In one variation, the supplementation with the disclosed compositions in ESRD patients with Calcific Uremic Arteriolopathy (Calciphylaxis) will reduce the time of wound healing by preventing calcification of new blood vessels and restoring blood flow: Skin Biopsies: To confirm that supplementation of the disclosed compositions prevents the development of small vessel calcification and dermal ischemia, we may identify patients with calciphylaxis confirmed by dermal skin biopsy and randomize patients to treatment with menaquinone-7 or placebo. Clinical Endpoints may include the following: 1) Time to Wound Vacuum therapy withdrawal and 2) time for wound healing defined as the time needed for a 50% reduction in collective the surface area of all calciphylaxis wounds.

Histopathologic Endpoints: Comparison of Diagnostic dermal biopsy with Protocol repeat dermal biopsy after 12 weeks of Menaquinone-7 therapy. Change in the level of interstitial calcium deposition defined as the change in Von Kossa staining, which may be quantified by digital image color analysis. Dermal biopsies may be used to validate the biomarkers at the tissue level. This enables the confirmation of the preventive properties of MK-7 on early vascular calcification. The validation of these biomarkers at the tissue will also enable clinicians to utilize the biomarkers as means to track clinical responsiveness. Calcification of microvasculature precedes development of CUA lesions. The level of calcification will be quantified by Von Kossa calcium staining in the peripheral tissue and normalized as calcium content per unit area. We may use the Von Kossa as a means of confirming the preventive properties of MK-7 on the development of vascular calcification.

In one variation, the supplementation of the disclosed compositions in ESRD patients with Calcific Uremic Arteriolopathy (Calciphylaxis) will reduce the time of wound healing by normalizing carboxy Protein C levels in the dermis and preventing primary thrombosis of dermal blood vessels. Accordingly, in one variation, the supplementation or administration of the disclosed compositions in diabetic patients will prevent the development of vascular dementia by preventing calcification and development of small vessel vasculopathy.

Alzheimer's Disease, Apoptosis and Treatment of Cancer:

Alzheimer's Disease (AD) is a devastating neurodegenerative disorder. Its sporadic forms affect an elderly population (sharp increase in incidence at >75 years of age), in addition, there are various familial forms with an onset of the disease in the fourth or fifth decade of life. AD is characterized by the presence of extracellular senile plaques, and intracellular neurofibrillar tangles in patient's brains. The core constituent of the senile plaques are small, 4 kDa amyloid peptides, which are generated by the proteolytic processing of a large transmembrane protein, amyloid precursor protein (APP). Cleavage of APP by beta-secretase (BACE-1) releases the soluble APP-beta fragment, while the 99-amino acid long C-terminus remains tethered to the membrane. This C-terminal fragment is subsequently proteolytically processed by gamma-secretase (a membrane multi-enzyme complex) to generate amyloid peptides of various length, predominantly 40 and 42 amino acids long (Hardy J. et al. (2002) Science: 297 (5580):353-356) in one embodiment, the treatment of a disease or condition, using the composition as disclosed herein, is mediated by BACE-1, BACE-2 or cathepsin D activity, such as Alzheimer's Disease, mild cognitive impairment, impaired glucose tolerance or type 2 diabetes. In one variation, the disclosed method may be employed for the treatment of calcification in the brain.

It has been shown that β-amyloid (Aβ) leads to neuronal death by promoting apoptosis and also by direct toxicity. Hadipour, E. et al. *Vitamin K2Protects PC12 Cells against Aβ (1-42) and $H_2O_2$-Induced Apoptosis via P38MAP Kinase Pathway*. Nutr. Neurosci. 2020, 23, 343-352. Neurotoxicity occurs through a variety of mechanisms, including the disruption of calcium homeostasis, oxidative stress and mitochondrial dysfunction. In PC12 cells derived from a rat pheochro-mocytoma, vitamin K2 prevented neuronal death resulting from Aβ(1-42), the most neuro-toxic form of Aβ. Experimentally, it was also demonstrated that when cells were exposed to either hydrogen peroxide ($H_2O_2$) or Aβ(1-42), the cells that were pretreated with vitamin K2 exhibited significantly less apoptosis. Pretreatment with vitamin K2 also decreased the amount of apoptosis signaling proteins, including a lower Bax/Bcl-2 ratio, reduced the presence of reactive oxygen species (ROS), and increased the amount of glutathione, which is an anti-oxidant. Yagami, T. *Gas6 Rescues Cortical Neurons from Amyloid β Protein-Induced Apoptosis* Neuropharmacology 2002, 43, 1289-1296. The researchers determined that the inactivation of the p38 MAP kinase pathway was a mechanism for the potential protective role of VK2 in Alzheimer's disease (Aβ).

The researchers observed that an increase in the concentration of vitamin K2VK2, cells exhibited prolonged survival presumably because of their protection against Aβ-induced neuronal death. It was also noted that this effect was reversible upon the addition of warfarin, which prevents vitamin K-dependent carboxylation. VK2 was observed to reduce the number of ROS in a dose-dependent manner and, at a concentration of 10 mcmol/L, decreased by 2.5-fold the activity of caspase-3, an enzyme that mediates Aβ-induced apoptosis. The authors also found that Gas6 plays a role in VK2 protection against AR cytotoxicity; which confirmed that, based on the measured Ca(2+) influx, chromatin condensation, and DNA fragmentation as markers for AR neurotoxicity and apoptosis in rat embryo neuronal cell cultures. Gas6 inhibited the influx of Ca(2+) in a dose-dependent manner and significantly decreased the amount of chromatin condensation and DNA fragmentation caused by Aβ. Accordingly, there is a clear correlation between the antioxidant properties and anti-apoptotic properties of vitamin K2, which is associated with the process of programmed cell death as an effective mechanism associated with the treatment of cancers.

Targeting apoptosis is also effective for various types of cancer, as apoptosis evasion is a hallmark of cancer. Apoptosis is also nonspecific to the cause or type of the cancer. See Villa-Pulgarin J. A. et al. *Mitochondria and lipid raft-located $F_oF_1$-ATP synthase as major therapeutic targets in the antileishmanial and anticancer activities of ether lipid edelfosine*. PLoSNegl. Trop. Dis. 2017; 11:e0005805. doi: 10.1371/journal.pntd.0005805; Elmore S. Apoptosis: A review of programmed cell death. *Toxicol. Pathol.* 2007; 35:495-516. doi: 10.1080/01926230701320337.

Vitamin K2 has also been used in clinical applications to supplement the treatment of cancers. XV, F. et al., *Research Progress on the anticancer effects of vitamin K2* (Review). Oncol. Lett. 2018, 15, 8926-8934. In addition, vitamin K2 supplementation have been found to prevent the growth and metastasis of multiple cancer lines. See Xia, J. et al., *The role of PKC isoforms in the inhibition of NF-KB activation by vitamin K2 in human hepatocellular carcinoma cells*. J. Nutr. Biochem. 2012m 23, 1668-1675; Showalter, S. L. et al., *Naturally occurring K vitamins inhibit pancreatic cancer cell survival through a caspase-dependent pathway*. J. Gastroenterol. Hepatol. 2010, 25, 738-744. Enomoto, M. et al. *Vitamin K2-induced cell growth inhibition via autophagy formation in cholangiocellular carcinoma cell lines*. Int. J. Mol. Med. 2007, 20, 801-808; Jinghe, X., *Vitamin K and hepatocellular carcinoma: The basic and clinic*. World J. Clin. Cases 2015, 3, 757-764. Sada, E. et al. *Vitamin K2 modulates differentiation and apoptosis of both myeloid and erythroid lineages*. Eur. J. Haematol. 2010, 85, 538-548; Yaguchi, M. et al., *Vitamin K2 and its derivatives induce apoptosis in leukemia cells and enhance the effect of all-trans retinoic acid*. Leukemia 1997, 11, 779-787.

In fact, it was determined that the intake of MK-4 and MK5 to MK-9 was inversely associated with cancer mortality. In particular, in a male cohort study, there was an inverse association between the incidence of advanced protate cancer and MK intake, particularly MK-5 to MK-9. Nimptsch, K. et al. (2008) *Dietary intake of vitamin K and risk of prostate cancer in the Heidelberg cohort of the European Prospective Investigation into Cancer and Nutrition* (EPIC-Heidelberg). Am. J. Clin. Nutr. 87, 985-992. Nimptsch, K. et al. (2010) *Dietary vitamin K intake in relation to cancer incidence and mortality: results from the Heidelberg cohort of the European Prospective Investigation into Cancer and Nutrition* (EPIC-Heidelberg). Am. J. Clin. Nutr. 91, 1348-1358. In a nested case-control follow-up study, undercarboxylation of osteocalcin (a marker of inadequate vitamin K status) was significantly higher in cases with advanced or high-grade prostate cancer versus controls. Nimptsch, K. et al. (2009) *Serum undercarboxylated osteocalcin as biomarker of vitamin K intake and risk of prostate cancer: a nested case-control study in the Heidelberg cohort of the European Prospective Investigation into Cancer and Nutrition*. Cancer Epidemiol. Biomark. Prev. 18, 49-56. Wang et al. also reported a positive association between the intake of MKs and the risk of breast cancer incidence and death, particularly for luminal-like, triple-negative, and early-stage disease. Wang, K. et al. (2021) *Vitamin K intake and breast cancer incidence and death: results from a prospective cohort study*. Clin. Nutr. 40, 3370-3378. Accordingly, in one variation, there is provided a method for the treatment of cancer, such as prostate cancer, by the administration of a therapeutically effective amount of the disclosed composition to control or reduce the high level of undercarboxylation of osteocalcin.

Pharmaceutical compositions disclosed herein may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, 5% dextrose in water or buffered sodium or ammonium acetate solution. Such formulations are especially suitable for parenteral administration but may also be used for oral administration. Excipients, such as polyvinylpyrrolidinone, gelatin, hydroxycellulose, acacia, polyethylene glycol, mannitol, sodium chloride, or sodium citrate, may also be added. Alternatively, these compositions may be encapsulated, tableted, or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols, or water. Solid carriers include starch, lactose, calcium sulfate, dihydrate, terra alba, magnesium stearate or stearic acid, talc, pectin, acacia, agar, or gelatin. The carrier may also include a sustained release material such as glyceryl monostearate or glyceryl distearate, alone or with a wax. The amount of solid carrier varies but may be between about 20 mg to about 1 g per dosage unit. The pharmaceutical preparations are made following the conventional techniques of pharmacy involving milling, mixing, granulation, and compressing, when necessary, for tablet forms; or milling, mixing, and filling for hard gelatin capsule forms. When a liquid carrier is used, the preparation will be in the form of a syrup, elixir, emulsion, or an aqueous or non-aqueous suspension. Such a liquid formulation may be administered directly p.o. or filled into a soft gelatin capsule. Suitable formulations for each of these methods of administration may be found in, for example, *Remington: The Science and Practice of Pharmacy*, A. Gennaro, ed., 20th edition, Lippincott, Williams & Wilkins, Philadelphia, Pa.

As disclosed herein, the disclosed compositions may include a solubility enhancer or solubilizer (or emulsifier) selected from oleic acid, Kolliphor® EL (polyoxyl castor oil or Cremophor EL), Vitamin E TPGS (D-α-tocopherol polyethylene glycol-1000 succinate), Maisine® CC (glyceryl monolinoleate), Gelucire® 44/14 (lauroyl polyoxyl-32 glycerides), Miglyol® 812N (esters of saturated coconut and palm kernel oil-derived caprylic fatty acids and glycerin), Plurol® Oleique (Polyglyceryl-6 Dioleate), Lauroglycol™ 90 (propylene glycol monolaurate (type II), Labrasol® (Caprylocaproyl polyoxyl-8 glycerides), Kolliphor® EL (polyoxyl castor oil), Captisol® (SBE-beta-cyclodextrin), Encapsin™ HPB (hydroxypropylbeta-cyclodextrin), Peceol™ (glycerol/glyceryl monooleate (type 40)), sodium deoxycholate, deoxycholic acid, Labrafil® M2125CS (linoleoyl Polyoxyl-6 glycerides) and medium-chain mono- and diglycerides.

In addition to the exemplary embodiments, aspects and variations described above, further embodiments, aspects and variations will become apparent by reference to the drawings and figures (FIGS.) and by examination of the following descriptions.

DETAILED DESCRIPTION OF THE INVENTION

Definitions

Unless specifically noted otherwise herein, the definitions of the terms used are standard definitions used in the art of organic synthesis and pharmaceutical sciences. Exemplary embodiments, aspects and variations are illustratived in the figures and drawings, and it is intended that the embodiments, aspects and variations, and the figures and drawings disclosed herein are to be considered illustrative and not limiting.

As used herein, the term "composition" is used interchangeably with "formulation" and refers to the nanoparticles as described herein.

As used herein, the term "emulsion" generally refers to a mixture of two normally unmixable liquids in which one is colloidally suspended in the other (defining a dispersed phase). The particle sizes of the dispersed phase in an emulsion generally lie between a few hundred nanometers and a few tens of micrometers. Where the micelles are sufficiently small, the emulsion is essentially clear. Typically, the emulsion will appear clear to the human eye, when the micelles have a median particle size of less than 100 nm. In one example, the micelles in the emulsions of the present application have median particle sizes below 60 nm. In a typical example, micelles formed in the emulsion have a median particle size between about 30 to 40 nm, 20 and 30 nm, 15 to 20 nm or about 10 to 15 nm. In another example, the emulsion is stable, which means that separation between the aqueous phase and the lipophilic component does essentially not occur (e.g., the emulsion stays clear). A typical aqueous medium, which is used in the emulsions of the present application, is water, which may optionally contain other solubilized agents, such as pharmaceutically acceptable excipients.

As used herein, the term "emulsifier" is used interchangeably with the terms "surfactant" and "solubilizing agent", and as defined herein.

As used herein, the term "nanoparticle" refers to a particle having at least one dimension that is less than 1,000 nm, as determined by a Dynamic Light Scattering particle sizer, for example. Other methods known in the art include disc centrifugation, nanoparticle tracking analysis, tunable resistive pulse sensing, or electron microscopy.

The term "micelle" is used herein according to its art-recognized meaning and includes all forms of micelles, including, for example, spherical micelles, cylindrical micelles, worm-like micelles and sheet-like micelles, and vesicles, formed in water, or mostly water.

"Pharmaceutically acceptable salts" means salt compositions that is generally considered to have the desired pharmacological activity, is considered to be safe, non-toxic and is acceptable for veterinary and human pharmaceutical applications. Such salts include acid addition salts formed with inorganic acids such as hydrochloric acid, hydrobromic acid, sulfuric acid, phosphoric acid, and the like; or with organic acids such as acetic acid, propionic acid, hexanoic acid, malonic acid, succinic acid, malic acid, citric acid, gluconic acid, salicylic acid and the like.

"Poorly soluble drugs", as generally used herein, means a drug having a solubility of 100 mg/mL or less in water. Another definition may include a drug that has a solubility of less than 1 mg/L over the physiological pH range.

A "stable" formulation or a "stable" composition is one in which the vitamin K2 essentially retains at least one of its physical stability, chemical suability, and biological activity upon storage, by at least 6 months or at least 12 months at room temperatures. Various analytical techniques for measuring drug particle stability are available in the art, such as Jones, A. et al. Adv. Drug Delivery Rev.; such as noted at 10: 29-90 (1993). In one aspect, the stability can be measured at a selected temperature for a selected period of time.

As used herein, the term "suspension" generally refers to a dispersion of fine particles in a liquid.

"Therapeutically effective amount" means an amount of a compound or composition that elicits any of the biological effects listed in the specification.

EXPERIMENTAL

Figure 1:
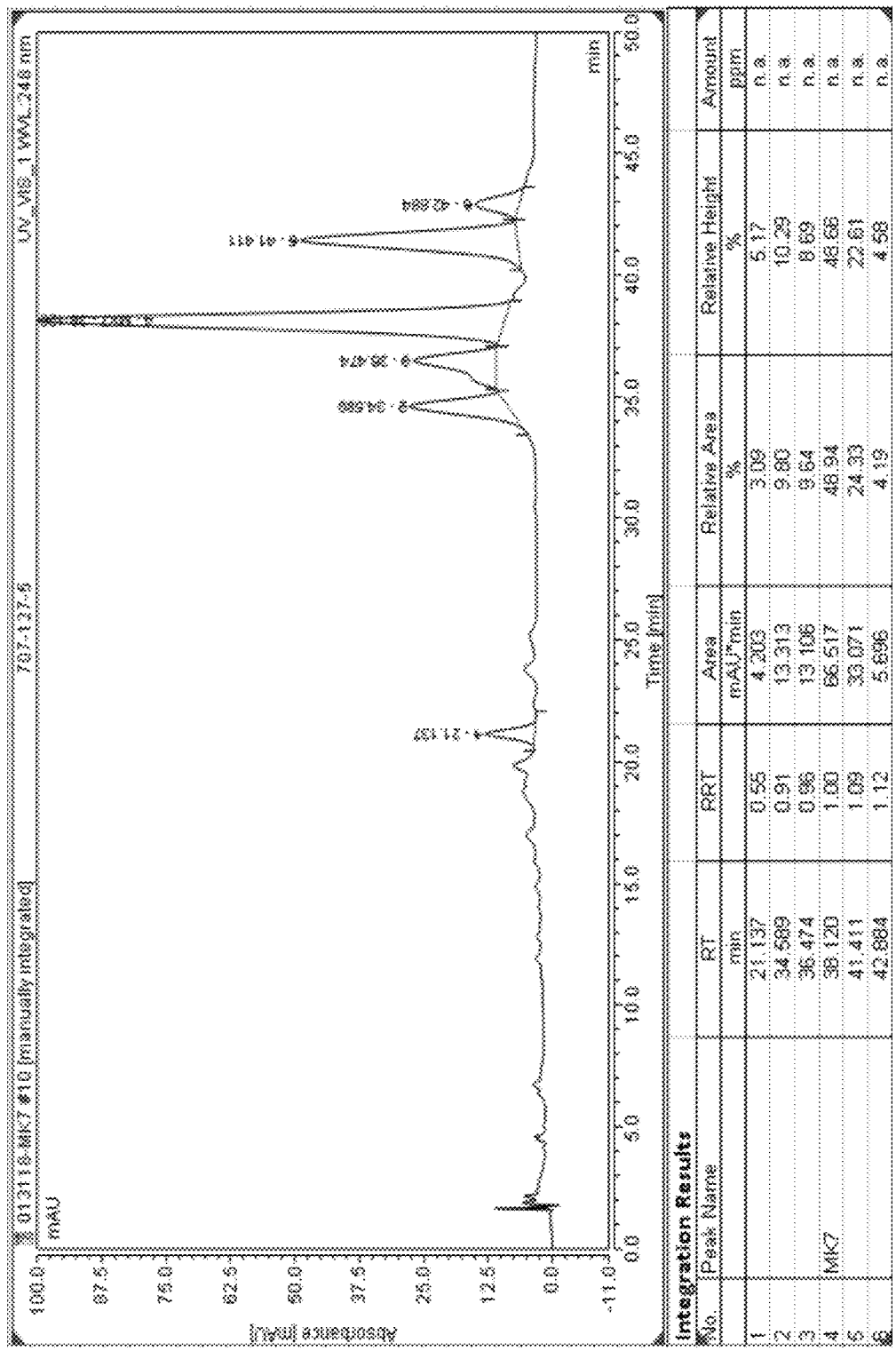
FIG. 1 is a representation of a chromatogram of menaquinone-7 and its regioisomer shown with a ratio of 3:1, as determined by $^1$H NMR.
Figure 2:
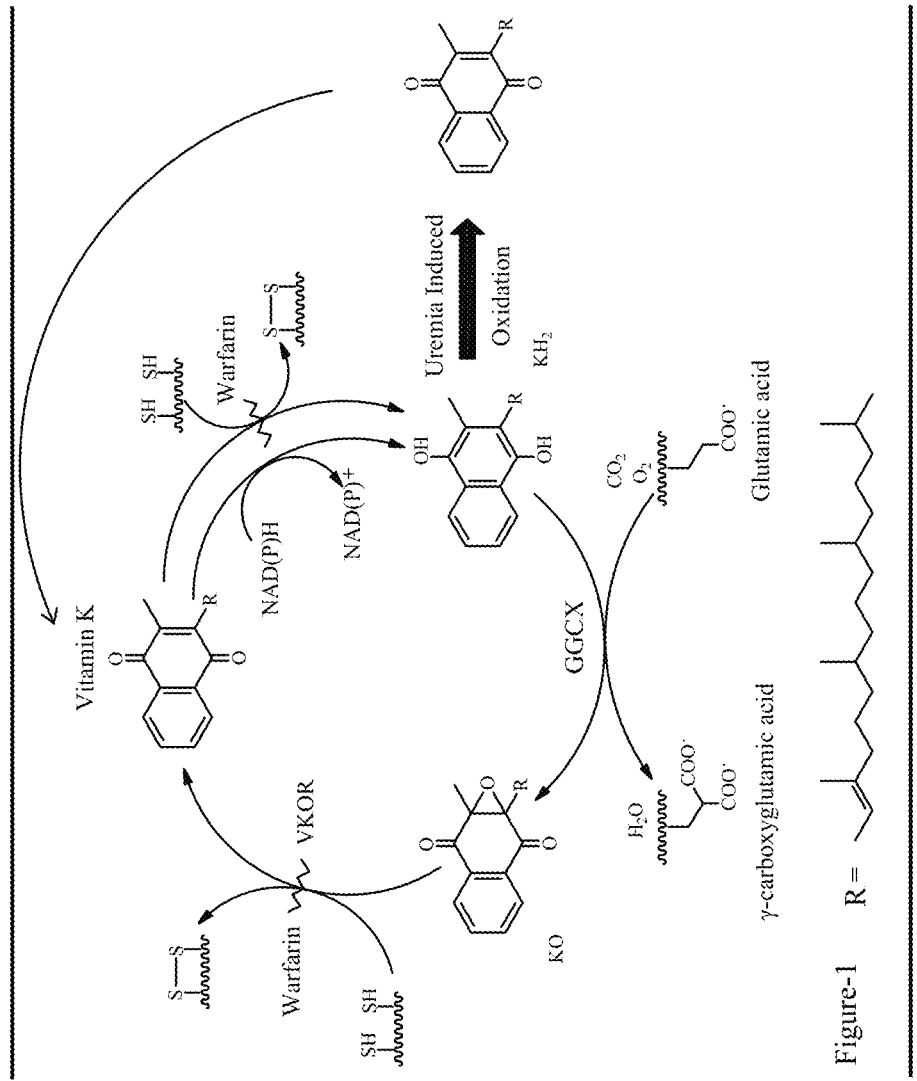
FIG. 2 is a scheme showing the uremia and dialysis induced oxidation of KH2 functional carboxylation of vitamin K dependent proteins.
Figure 3:
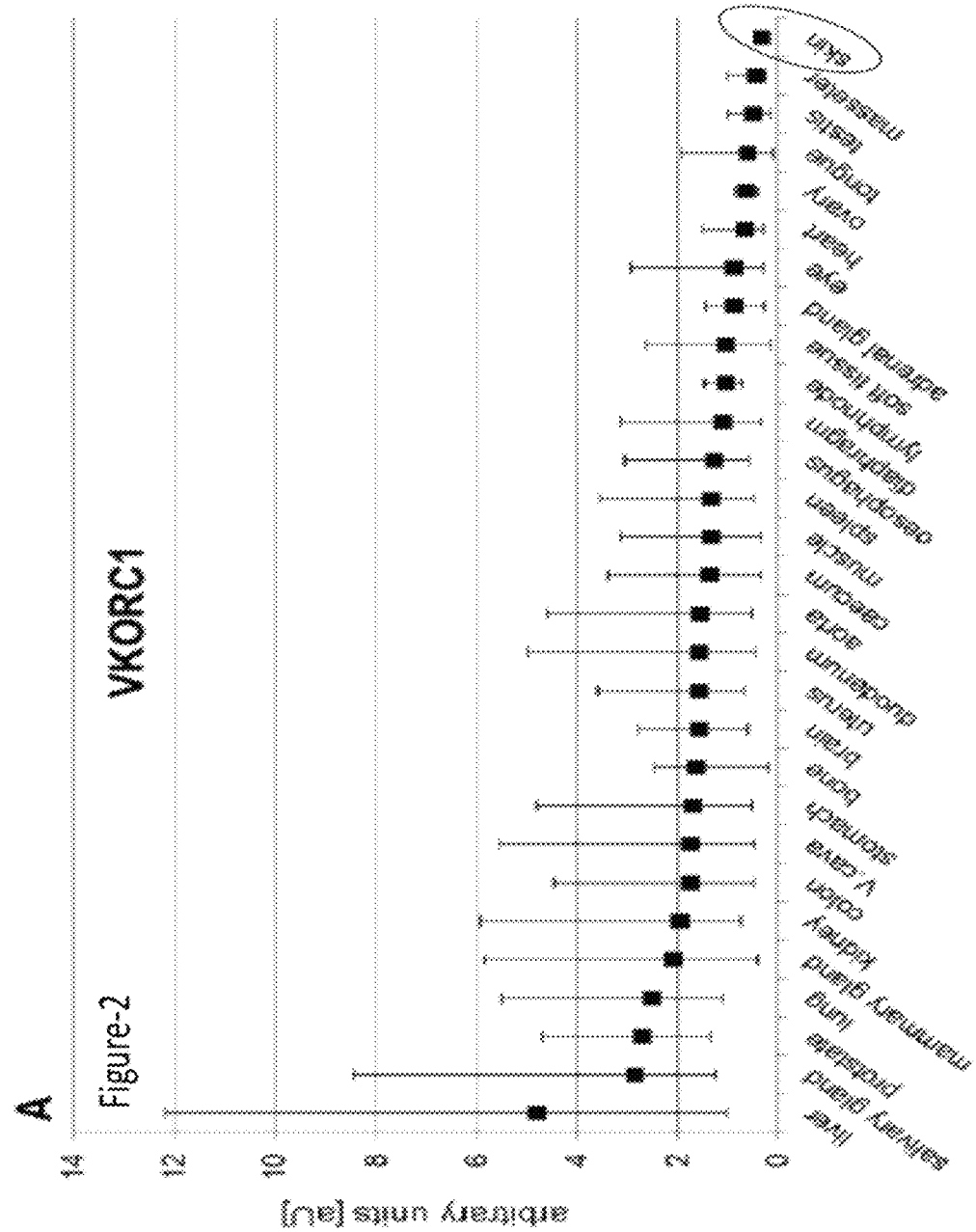
FIG. 3 is graph showing the VKORC1 in arbitrary units and specific tissues.
Figure 4:
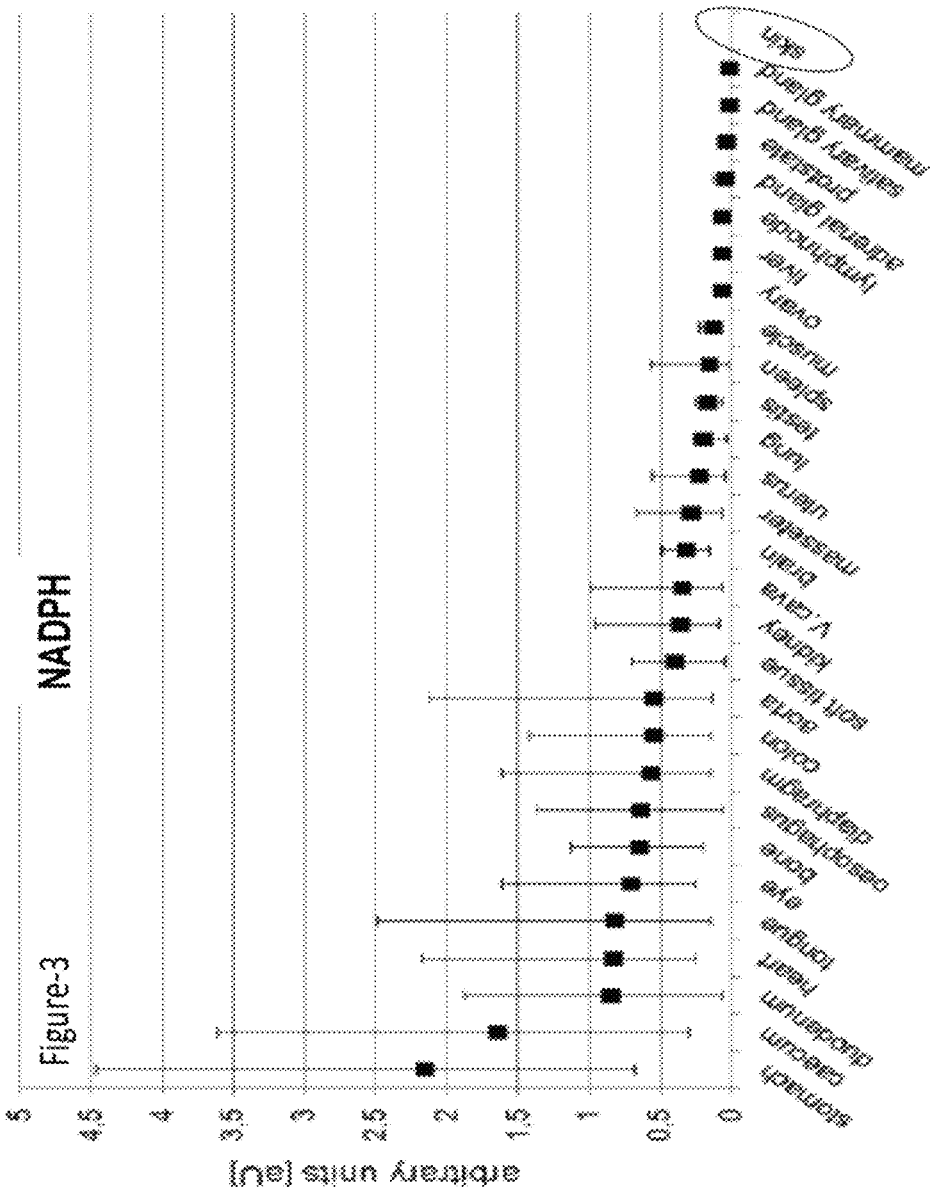
FIG. 4 is a graph showing the NADPH in arbitrary units and specific tissues.
Figure 5:
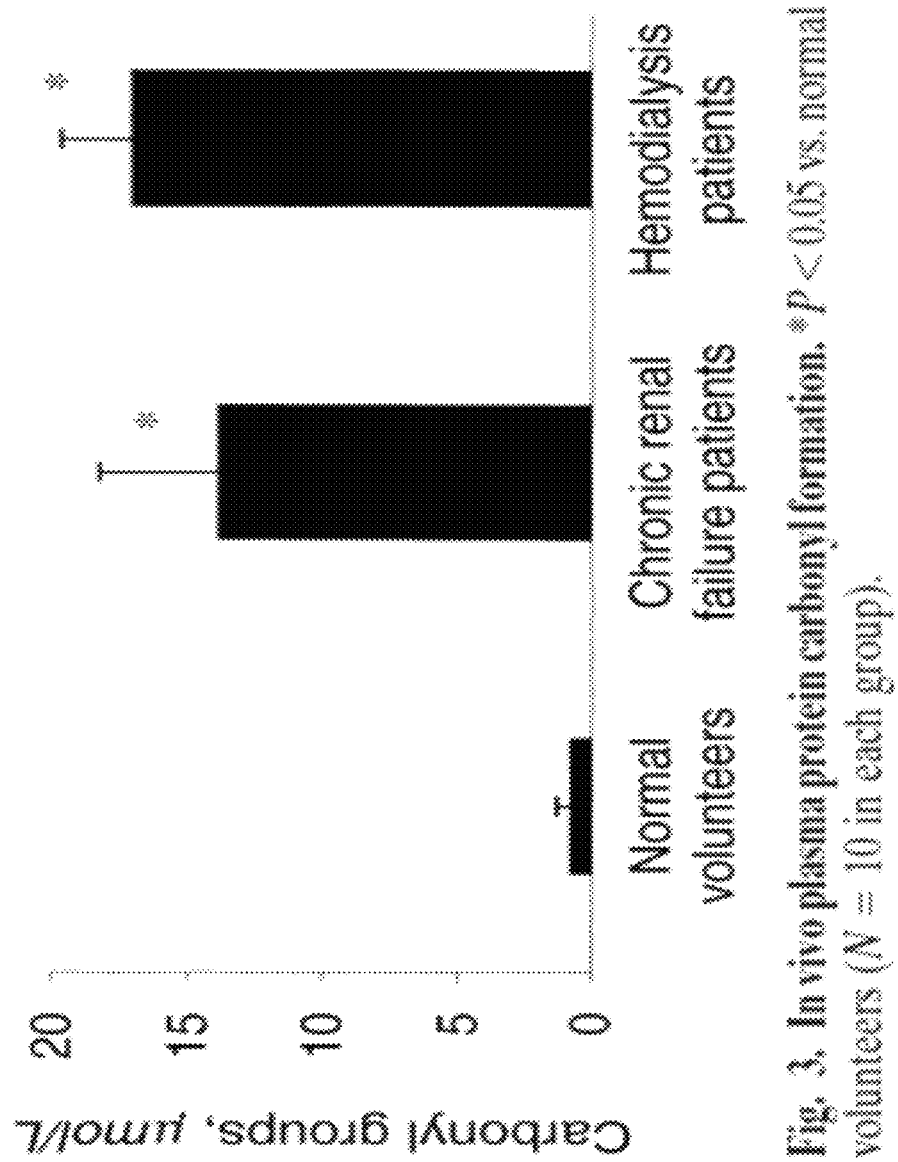
FIG. 5 is a graph showing CKD and ESRD patients exhibit a higher percentage of carbonyl proteins compared to normal controls.

1. Dissolution Testing of MK-7 Nanosuspension in Fed State Simulated Intestinal Fluid (FeSSIF).

Material

MK-7—Anthem Bioscience lot A012220081
MK-7 nanosuspension—F-10 lot LPI 461-1-10
Sodium Deoxycholate—SAFC lot SLBT2846
Deionized water—Bamstead E-Pure filtration system
Zirconium milling beads, 0.4 mm—Netzsch lot #1310508
FeSSIF, pH 5—Prepared by LPI
Polypropylene tubes, 1.5 mL with screw cap; General lab supplies Equipment Beadbeater homogenizer (bench scale)
Vortexer (bench scale)
Analytical Balance
HPLC with variable wavelength UV detector—Agilent 1100 series
Dynamic Light Scattering particle sizer—Malvern Zeta-Sizer
Dissolution apparatus—Vankel 7000

MK-7 (menaquinone-7, API) was suspended in an aqueous vehicle containing wetting agent sodium deoxycholat. The API concentration was 4% and the wetting agent concentration was 0.4% w/w. The API particles were milled to a particle size of 155 nm using zirconium milling beads and high shear Beadbeater mixing. The dissolution of the nanosuspension was tested at a concentration of 0.01 mg/mL, in triplicate, in pH 5 Fed State Simulated Intestinal Fluid (FeSSIF). These results were compared to the dissolution of the API "as is" (MK-7—Anthem Bioscience), tested under the same conditions.

TABLE 1

COMPOSITION of MK-7 Nanosuspension (F-10)

| Component | % w/w |
|---|---|
| MK-7 | 4.00 |
| Sodium deoxycholate | 0.50 |
| Deionized water | QS to 100% |

Procedure

Part 1. Nanosuspension Preparation Process

1. Set-up equipment and materials in a room lit by a low wavelength yellow light. 2. Add 0.040 g of MK-7 and 0.005 g sodium deoxycholate to a 1.5 mL polypropylene tube with a screw cap. 3. QS to 1 g with deionized water. 4. Vortex for approximately 1 minute to completely dissolve the sodium deoxycholate and uniformly suspend the MK-7. 5. Add 0.4 g of 0.4 mm zirconium beads to the suspension. 6. Cover the suspension tube with aluminum foil to protect MK-7 from light. 7. Place the tube in an ice bath. 8. Set-up a Beadbeater mixer in a −20° C. freezer. 9. In a −20° C. freezer, use the Beadbeater to mix the suspension for twelve (12) intervals of five minutes each. Monitor temperature of the suspension with laser thermometer, and maintain the suspension temperature below 30° C. 10. Measure the Particle Size by using dynamic light scattering by diluting 10 μL of the suspension in 950 μL of 0.5% sodium deoxycholate vehicle in a transparent cuvette. 11. Confirm the particle size is less than 300 nm. 12. Measure the assay and impurities, in triplicate, by RP-HPLC using amber glassware. 14. Store the nanosuspension at 2-8° C.

TABLE 2

HPLC METHOD

| Mobile Phase | MPA: 100% Deionized water, MPB: 100% ethanol | |
|---|---|---|
| Column | Phenomenex Kinetex C18 4.6 × 100 mm 2.6 μm p/n 00D-4462-E0 | |
| Column temperature (° C.) | 25 | |
| Detection wavelength (nm) | 268 | |
| Injection volume (μL) | 10 | |
| Autosampler temperature (° C.) | Ambient | |
| Flow (mL/min) | 0.7 | |
| Run time (min) | 30 | |
| Mode: isocratic | MPA (%) | MPB (%) |
| | 10 | 90 |

Results

TABLE 3

Data for MK-7 Nanosuspension

| Particle Size (nm) | PDI* | Assay (mg/mL) | Purity (% Area) |
|---|---|---|---|
| 156 | 0.138 | 34.1 | 99.5+ |

*uniformity of particle size distribution scaled 0-1, where 0 is most uniform

Figure 6:
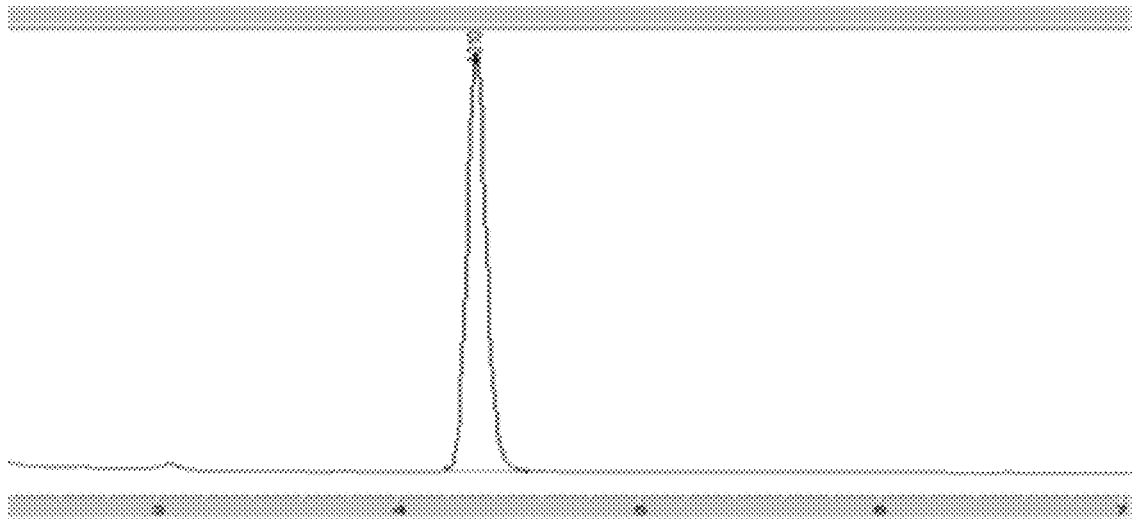
FIG. 6. shows an exemplary chromatogram of F-10 Nanosuspension.

FIG. 6 shows an exemplary Chromatogram of F-10 Nanosuspension, in which all impurity detected are less than 0.0500 total peak area.

TABLE 3

Initial Data for MK-7 Nanosuspension

| Particle Size (nm) | PDI* | Assay (mg/mL) | Purity (% Area) |
|---|---|---|---|
| 156 | 0.138 | 34.1 | 99.5+ |

*uniformity of particle size distribution scaled 0-1, where 0 is most uniform

Figure 7:
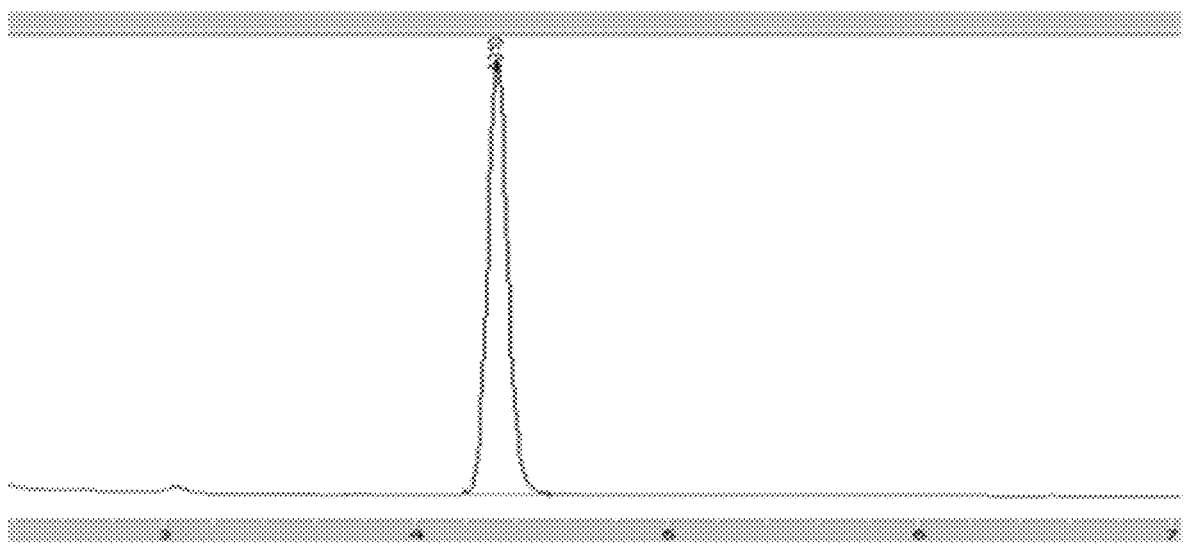
FIG. 7. shows an exemplary chromatogram of F-10 Nanosuspension.

FIG. 7 shows an exemplary Chromatogram of F-10 Nanosuspension, in which all impurity detected are less than 0.05% total peak area.

Part 2. In Vitro Release Testing

1. Clean dissolution system with DI water. Prepare FeSSIF: 2. Fill three (3) vessels with 500 mL of FeSSIF media and heat to 37° C. 3. Set up the following dissolution conditions:

TABLE 4

Dissolution Parameters

| Apparatus | Speed (RPM) | Temp (° C.) | Time points (min) | MK-7 Drug Load (mg/mL) | Media (500 mL) |
|---|---|---|---|---|---|
| Paddle | 75 | 37 | 5, 10, 15, 30, 45, 60 | 0.01 | FeSSIF |

4. Vortex suspension x for approximately one minute so that it is uniform. Weigh three (3) aliquots of 0.15 g of the 4% nanosuspension into a tared syringe to give a target 100% dissolution concentration of 0.01 mg/mL. Record weight. 5. Add weighed suspension directly to each vessel. 6. Start at Timer. 7. After five minutes, manually pull up 3 mL from each dissolution vessel in a syringe. 8. Attach a 0.2 μm filter to the syringe. 9. Transfer 2 mL of the dissolution sample back into the vessel. 10. Transfer the final 1 mL of sample to an amber HPLC vial and crimp seal. 11. Repeat Steps #8-11 at 10, 15, 30, 45 and 60 mins. 12. After the 60-minute time-point, mix each vessel for 5 minutes with a high shear mixer. 13. Repeat Step #8-11 and label this sample as 'infinity'. 14. Run samples on HPLC 10 minutes HPLC method with replicate HPLC standard solutions.

TABLE 5

% Dissolution Data of MK-7 API and Nanosuspension in FeSSIF at 0.01 mg/mL Drug Load.

| Timepoint (minute) | API % Dissolution (Avg of n = 3) | F-10% Dissolution (Avg of n = 3) |
|---|---|---|
| 0 | 0 | 0.0 |
| 10 | 96.7 | 8.2 |
| 15 | 97.3 | 18.1 |
| 30 | 97.8 | 16.6 |
| 45 | 97.7 | 16.4 |
| 60 | 95.7 | 15.8 |
| Infinity | 97.0 | 10.7 |

Figure 9A:
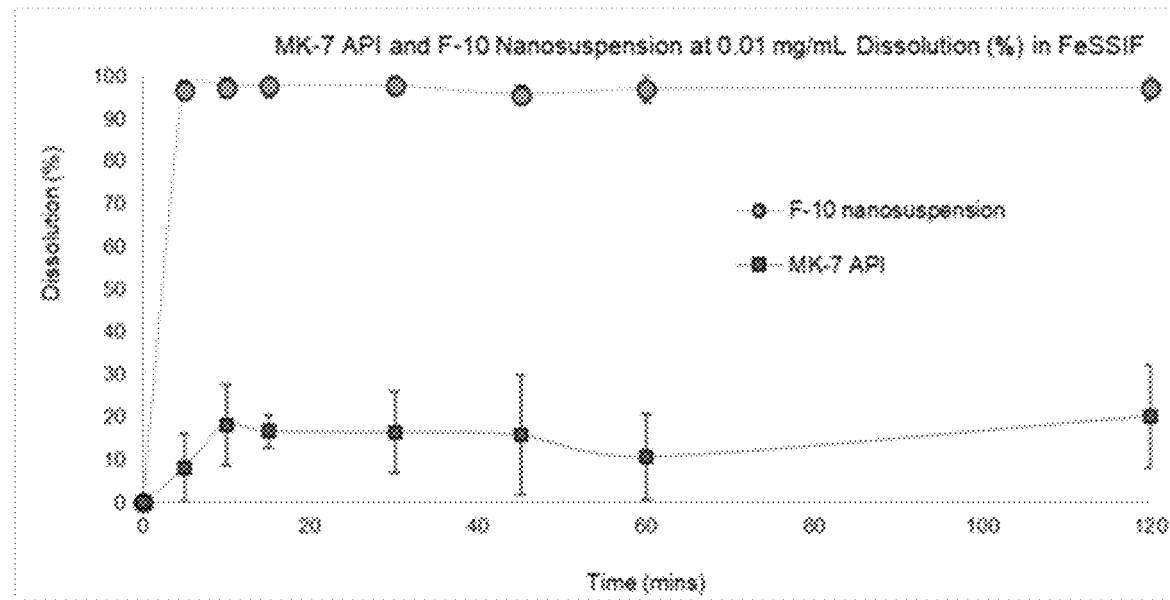
FIGS. 9A and 9B show % Dissolution Profile of MK-7 API and Nanosuspension in FeSSIF.
Figure 9B:
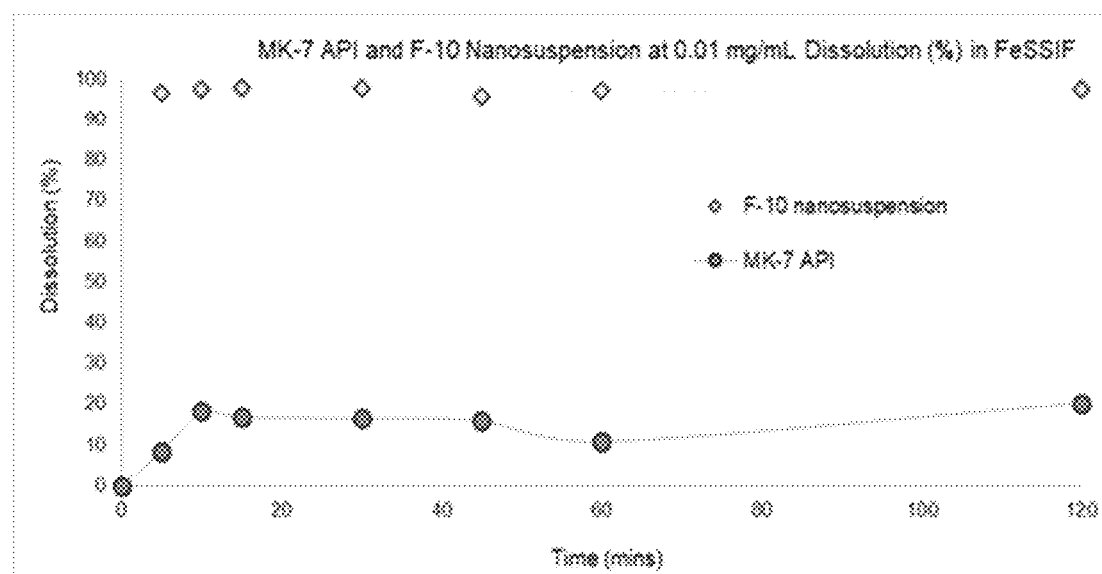

FIGS. 9A and 9B show % Dissolution Profile of MK-7 API and Nanosuspension in FeSSIF.

Nano-milled particles dissolve at a significantly higher rate and amount that API particles 'as is' or MK-7 API.

2. Summary Dissolution Testing of MK-7 Nanosuspension in Fed State Simulated Intestinal Fluid (FeSSIF).

MK-7 (menaquinone-7, API) was suspended in an aqueous vehicle containing wetting agent, sodium deoxycholate.

The API concentration was 4% and the wetting agent concentration was 0.4% w/w. The API particles were milled to a particle size of 156 nm by use of zirconium milling beads and high shear Beadbeater mixing. The dissolution of the nanosuspension was tested at a concentration of 0.01 mg/mL, in triplicate, in pH 5 FeSSIF. These results were compared to the dissolution of the API 'as is', tested under the same conditions.

Materials

MK-7—Pharmaquinone lot API2203-01; MK-7 nanosuspension—F-10 lot LPI 461-1-10; Sodium Deoxycholate—SAFC lot SLBT2846; Deionized water—Barnstead E-Pure filtration system; Zirconium milling beads, 0.4 mm—Netzsch lot #1310508; FeSSIF, pH 5—Prepared by LPI.

Composition of MK-7 Nansuspension (F-10)

| Component | % w/w |
|---|---|
| MK-7 | 4.00 |
| Sodium deoxycholate | 0.50 |
| Deionized water | QS to 100% |

Procedure

Clean dissolution system with DI water. Fill 3× vessels with 500 mL of FeSSIF media and heat to 37° C. Set up the following dissolution conditions:

| Apparatus | Speed (RPM) | Temp (° C.) | Timepoints (min) | Media (900 mL) |
|---|---|---|---|---|
| Paddle | 75 | 37 | 5, 10, 15, 30, 45 and 60 | FeSSIF |

Vortex suspension×1 minute so that it is uniform. Weigh 3×0.15 g portions of nanosuspension into a tared syringe to give a target 100% dissolution concentration of 0.01 mg/mL. Record weight. Add weighed suspension directly to each vessel. Start at Timer.

At 5 mins, manually pull up 3 mL from each vessel in a syringe. Attach a 0.2 μm filter to the syringe. Transfer 2 mL of the aliquot back into the vessel. Transfer the final 1 mL of aliquot to an HPLC vial and crimp seal. Repeat Steps #8-11 at 10, 15, 30, 45 and 60 mins. After the 60-minute time-point, mix each vessel for 5 minutes with a high shear mixer. Repeat Step #8-11 and label this sample as 'infinity'.

Run samples on HPLC 10-minute HPLC method with replicate HPLC STDs.

Initial MK-7 Nanosuspension Data

| Initial MK-7 Nanosuspension Data | | | |
|---|---|---|---|
| Particle Size (nm) | PDI* | Assay (mg/mL) | Purity (% Area) |
| 156 | 0.138 | 34.1 | 99.5+ |

*uniformity of particle size distribution scaled 0-1, where 0 is most uniform

Figure 8:
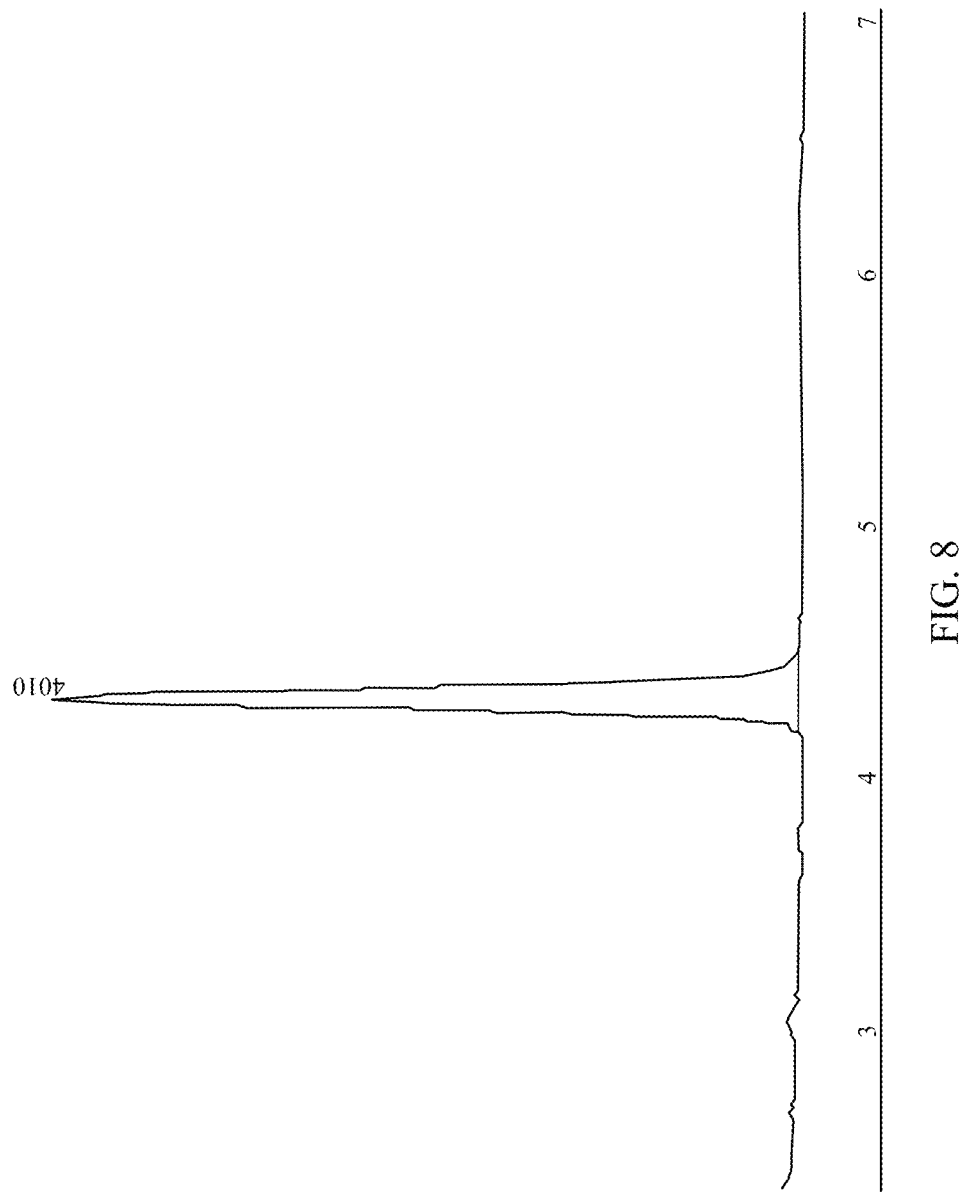
FIG. 8. shows an exemplary chromatogram of F-10 Nanosuspension.

FIG. 8 shows an exemplary Chromatogram of F-10 Nanosuspension, in which all impurity detected are less than 0.05% total peak area.

| % Dissolution Data of MK-7 API and Nanosuspension in FeSSIF. | | |
|---|---|---|
| Timepoint (minute) | API (Avg of n = 3) [0.0104 mg/mL] | F-10 (Avg of n = 3) [0.0104 mg/mL] |
| 0 | 0.0 | 0.0 |
| 5 | 4.1 | 100.4 |
| 10 | 9.1 | 101.0 |
| 15 | 8.3 | 101.5 |
| 30 | 16.6 | 101.5 |
| 45 | 7.9 | 99.4 |
| 60 | 5.3 | 100.7 |
| Infinity | 10.1 | 101.0 |

Figure 10:
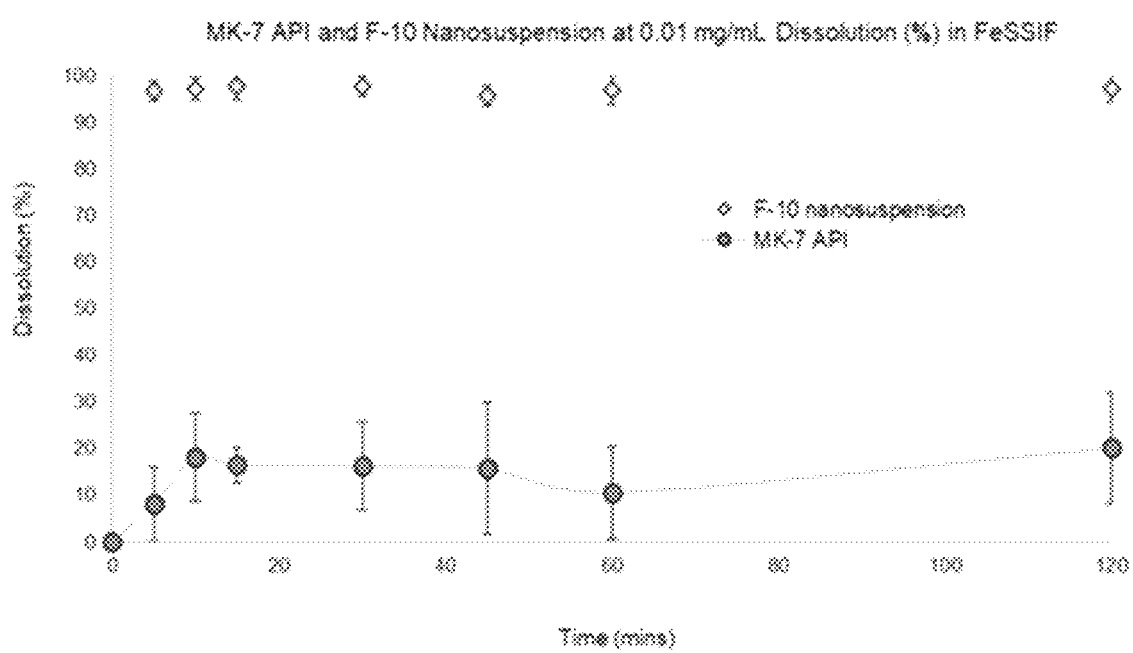
FIG. 10 shows % Dissolution Profile of MK-7 API and Nanosuspension in FeSSIF.

FIG. 10 shows % Dissolution Profile of MK-7 API and Nanosuspension in FeSSIF.

Nano-milled particles dissolve at a significantly higher rate and amount that API particles 'as is'. The nano-milling process is scaled up and the suspended nano-particles are removed from the suspension vehicle, dry and formulate into a fast dissolving tablet, and tested.

A menaquinol, such as MKH2-7, can be prepared from the corresponding menaquinone, such as MK-7, by reducing the menaquinone using conventional methods of reduction known in the art, including, for example, by reduction with a metal such as zinc and acetic acid, as described by Marchand et al. "Mild and Highly Selective Ultrasound-promoted Zinc/Acetic Acid Reduction of C=C Bonds in α,β-Unsaturated γ-Dicarbonyl Compounds," SYNTHESIS 1991 (3):198-200.

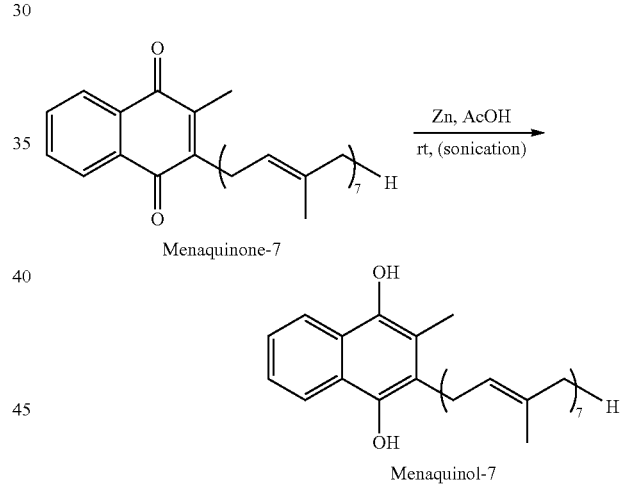

Menaquinone-7

Menaquinol-7

Accordingly, MK-7 (1 g, 1.54 mmol) may be dissolved in glacial acetic acid (15 mL), and powdered zinc (0.8 g, 12.3 mmol) is added. The resulting mixture is sonicated for 0.5 hour or the reaction mixture can be heated under reflux until reaction completion. The resulting mixture is filtered and the residue is washed with dichloromethane. The combined filtrates are concentrated in vacuo, to produce the pure reduction product. The procedure is performed under argon or nitrogen atmosphere. To stabilize MKH2-7 in the reduced form, MKH2-7 may be mixed with one or more antioxidants, such as vitamin C, a vitamin C ester (e.g., ascorbyl palmitate), and/or vitamin E. The resulting product may be processed under an inert atmosphere such as nitrogen or argon, and may be formulated in aninert or oxygen free medium, such as a capsule or softgel.

Similarly, MK-4 to MK-14 may be reduced to the corresponding MKH2-4 to MKH2-14 compounds in a similar manner.

General Process for Preparing Nano-Particle Emulsion of Menaquinone and Menaquinol in Water:

Note: As used herein, the terms "menaquinone and menaquinol" as employed describing an aqueous solution of menaquinone and/or menaquinol, may include or may contain primarily or mostly menaquinone; may include or may contain primarily or mostly menaquinol; or may include or contain a mixture of both menaquinone and menaquinol, in different ratios, that may contain a higher concentration of the menaquinone, or a higher concentration of the menaquinol.

Into a 50 mL glass RBF (or glass pressure reactor, or a Fisher or Porter bottle) with a large magnetic stir bar (or overhead stirrer) and equipped with pressure valve and inlet valve under nitrogen gas was added the solvent or solvent mixture. The valve is closed such that the content remains under nitrogen atmosphere. The RBF was heated in an oil bath at about 55 to 100° C., depending on the desired concentration of MK-7, the emulsifier or mixture of emulsifiers, and the solvent or solvent mixture. Once the solvent is heated to the desired temperature for at least 5 minutes, the emulsifier or co-emulsifiers are added by way of the inlet valve, into the solvent, and the inlet valve is closed. The resulting mixture is stirred for at least 5 minutes, until the resulting mixture is stirred and re-heated to the initial desired temperature.

Once the reaction mixture is re-heated up to the initial temperature, optionally, the desired amount of an antioxidant and optionally, the desired amount of a preservative, is added to the mixture. The resulting mixture is stirred and heated to the desired initial temperature, for at least 5 minutes.

Once the reaction mixture is stirred and again re-heated up to the initial temperature, MK-7 powder is added to the reaction mixture via the inlet valve under nitrogen, and the inlet valve is closed. The resulting mixture is stirred for at least 5 minutes; and the mixture is stirred and re-heated to the initial desired temperature for about 5 minutes to 60 minutes, depending on the amount or volume of the mixture in the RBF.

Depending on the desired heating temperature and the solvent or solvent mixture that is employed, the pressure in the glass RBF at the desired initial temperature may reach about 1 to 5 psi. After the desired amount of heating time, the resulting mixture is held at the desired temperature and a sample of the solution is removed from the RBF, via the sampling port, and checked for the desired NTU or clarity of solution. Once the desired NTU value is achieved, the resulting stirred mixture is slowly cooled to room temperature, over about 5 minutes to 15 minutes, depending on the volume of the reaction mixture. Once the mixture is cooled to room temperature, the resulting clear and slightly yellow-amber solution is stored at room temperature or in a refrigerator, at about 10-15° C.

The solvent employed may be pure water (distilled or deionized water), a mixture of water and an organic solvent such as DMSO, methanol, ethanol, isopropanol, methylisobutylketone, cyclodextrins, and N,N-dimethylacetamide, or mixtures thereof. In one variation, the organic solvent is DMSO. In another variation, the solvent mixture is water and DMSO.

Process for Preparing Nano-Particle Solid Emulsion of MK-7 in Water:

Into a 100 mL glass RBF with a large magnetic stir bar and equipped with pressure valve and inlet/outlet valve under nitrogen gas was added 22.0 g water. The valve was closed and the content was heated to a temperature of about 80° C. and stirred for 5 minutes. Kolliphor RH 40 (3.0 g) was added by way of the inlet valve, into the solvent, and the inlet valve was closed. The resulting mixture was stirred for at least 5 minutes, until the resulting mixture reached 80° C. MK-7 was added to the reaction mixture via the inlet valve under nitrogen, and the inlet valve was closed. The resulting mixture was heated and stirred for about 5 minutes until the mixture reached 80° C., and held at the same temperature for about 10 minutes.

A visual inspection of the reaction mixture shows a completed reaction process as the solution turns into a clear, and slightly yellow solution. A 1 mL sample of the solution was removed from the reaction mixture, via the sampling port, and the DLS (dynamic light scattering) analysis shows a particle size range of about 10-20 nm. The resulting stirred mixture was slowly cooled to room temperature, over about 5 minutes. The resulting solution was transferred to a capped glass container under nitrogen and stored at about 15° C. 0.5 mL Samples of the solution taken weekly shows that the solution remained clear, and the particle size (via DLS) remains substantially unchanged after 1 month at 32° C., but with some visual precipitation at approximately 1% as determined by quantitative HPLC.

Process for Preparing Nano-Particle Emulsion of MK-7 in Water and DMSO:

Into a 100 mL glass RBF with a large magnetic stir bar and equipped with pressure valve and inlet/outlet valve under nitrogen gas was added 11.0 g water and 11 g of DMSO. The valve was closed and the content was heated to a temperature of about 80° C. and stirred for 5 minutes. Kolliphor RH 40 (3.0 g) was added by way of the inlet valve, into the solvent, and the inlet valve was closed. The resulting mixture was stirred for at least 5 minutes, until the resulting mixture reached 80° C. MK-7 was added to the reaction mixture via the inlet valve under nitrogen, and the inlet valve was closed. The resulting mixture was heated and stirred for about 5 minutes until the mixture reached 80° C., and held at the same temperature for about 10 minutes.

A visual inspection of the reaction mixture shows a completed reaction process as the solution turns into a clear, and slightly yellow solution. A 1 mL sample of the solution was removed from the reaction mixture, via the sampling port, and the DLS (dynamic light scattering) analysis shows a particle size range of about 10-20 nm. The resulting stirred mixture was slowly cooled to room temperature, over about 5 minutes. The resulting solution was transferred to a capped glass container under nitrogen and stored at about 15° C. 0.5 mL Samples of the solution stored at about 32° C., taken monthly, over a period of 3 months shows that the slightly yellow solution remained clear, and the particle size (via DLS) remains substantially unchanged.

Process for Preparing Nano-Particle Emulsion of MK-9 in Water:

Into a 100 mL glass RBF with a large magnetic stir bar and equipped with pressure valve and inlet/outlet valve under nitrogen gas is added 22.0 g water. The valve is closed and the content was heated to a temperature of about 80° C. and stirred for 5 minutes. Kolliphor RH 40 (3.0 g) is added by way of the inlet valve, into the solvent, and the inlet valve is closed. The resulting mixture is stirred for at least 5 minutes, until the resulting mixture reached 80° C. MK-9 is added to the reaction mixture via the inlet valve under nitrogen, and the inlet valve is closed. The resulting mixture is heated and stirred for about 5 minutes until the mixture is heated to 80° C., and held at the same temperature for about 10 minutes.

A visual inspection of the reaction mixture shows a completed reaction process as the solution turns into a clear, and slightly yellow solution. A 1 mL sample of the solution is removed from the reaction mixture, via the sampling port, and the DLS (dynamic light scattering) analysis shows a particle size range of about 10-20 nm. The resulting stirred mixture is slowly cooled to room temperature, over about 5 minutes. The resulting solution is transferred to a capped glass container under nitrogen and stored at about 15° C. 0.5 mL Samples of the solution taken weekly shows that the solution remained clear, and the particle size (via DLS) remains substantially unchanged after 1 month at 32° C., but with some visual precipitation at approximately 1% as determined by quantitative HPLC.

Preparation and Stability of Nano-Particles of MK-7 in Water; Prepared by Microwave Heating:

Under nitrogen atmosphere, 5.00 g of MK-7 was added into a 50 mL conical flask equipped with a pressure stopper, and then 15 mL of Kolliphor EL was added and the resulting mixture formed a yellow cloudy suspension. The conical flask was sealed with the stopper and the conical flask was placed inside a microwave oven. The microwave oven was set on HIGH and the conical flask was heated to 80° C. for 2 minutes, where the yellow solution became homogeneous and formed a substantially clear-yellow solution. The conical flask was removed from the microwave and the pressure stopper was slowly removed under a nitrogen atmosphere. While the solution was still warm, at a temperature above 50° C., 35 mL of distilled water was added, all under a nitrogen atmosphere. The conical flask was re-sealed, and heated again in the microwave oven to about 80° C. for another 2 minutes to form the clear, homogeneous yellow solution. DLS analysis shows that the particle size distribution is about 10-15 nm. HPLC analysis shows that the MK-7 remained unchanged after 7 days at room temperature.

Administration of the Nanoparticle Compositions in Subjects at Risk for Development of Calciphylaxis:

This example describes the administration of the compositions of the present application to subjects at risk for development of calciphylaxis, but who have not yet developed the characteristic skin lesions of calciphylaxis. Risk factors to be considered include, but are not limited to, diabetes mellitus, obesity, hemodialysis, and prior treatment with warfarin (Nigwekar et al. (2016) *A Nationally Representative Study of Calcific Uremic Arteriolopathy Risk Factors*, J. AM. SOC. NEPHROL. 27(11):3421-9)). The administration of these compositions can result in protection of the subjects from skin lesions and a change in certain biomarker levels indicative of the prevention of the development of calciphylaxis.

Subjects at risk of development of calciphylaxis orally receive a selected composition of the present application at 0.1 mg, 3 mg, 5 mg or 10 mg once daily for at least 2 weeks, 4 weeks, 6 weeks, 8 weeks, 3 months, 6 months, 1 year, or indefinitely. The dosage form is a 0.1 mg, 3 mg, 5 mg or 10 mg pill or soft-gel capsule. Two 25 mg capsules are be administered once daily to the 50 mg dosage cohort. It should be noted that not all subjects with elevated risk factors for calciphylaxis will develop the characteristic skin lesions of calciphylaxis. The intent of treating with the compositions of the present application proactively (prior to a clinical diagnosis of calciphylaxis) is the prevention of lesion appearance. Thus, a drop in frequency of, or elimination of lesion appearances is contemplated to be a successful treatment.

Several biomarkers can be assessed to determine the efficacy of the compositions to be administered at the three dose levels. Exemplary biomarkers include PIVKA-II; uncarboxylated and total Matrix Gla Protein (MGP); uncarboxylated, carboxylated and total osteocalcin protein; uncarboxylated, carboxylated and total Protein C, osteoprotegerin, Fetuin A and hs-CRP. Blood samples are obtained to measure the biomarkers according to the following schedule. Blood sampling can occur during treatment on a weekly or monthly basis. The administration of the disclosed compositions results in (i) a decrease in PIVKA-II, which is indicative of slowing the progression of, arresting, or reversing, calciphylaxis, (ii) a decrease in uncarboxylated MGP, uncarboxylated osteocalcin, and/or uncarboxylated Protein C, which is indicative of slowing the progression of, arresting, or reversing calciphylaxis. Further, pulse wave velocity (PWV) can be measured to assess arterial compliance. Improved vascular compliance is indicative of slowing the progression of, arresting, or reversing calciphylaxis.

Administration of the Disclosed Compositions of the Application in Subjects Diagnosed with Calciphylaxis:

This example describes the administration of the disclosed compositions to subjects diagnosed with calciphylaxis. Typical symptoms include presentation of characteristic painful skin lesions (Nigwekar et al. (2015) *Calciphylaxis: Risk Factors, Diagnosis, and Treatment*. Am. J. Kidney Dis. 66:133-46). Definitive diagnosis of calciphylaxis is achieved via skin biopsy.

Subjects diagnosed with calciphylaxis orally receive the disclosed composition 0.1 mg, 3 mg, 5 mg or 10 mg once daily for at least 2 weeks, 4 weeks, 6 weeks, 8 weeks, 3 months, 6 months, 1 year, or indefinitely. The dosage form is a 0.1 mg, 3 mg, 5 mg or 10 mg tablet or soft-gel capsule. Two 25 mg capsules are administered once daily to the 50 mg dosage cohort.

The arrest of or decreases in lesion size and frequency is contemplated to be an indication of successful treatment. The administration of the disclosed compositions according to the foregoing will result in the arrest of or decrease in lesion size and frequency. Additionally, because calciphylaxis has a considerable mortality risk, increased overall survival time of diagnosed subjects will be an indication of treatment success. Furthermore, the administration of the disclosed compositions according to the foregoing will result in an increased overall survival time of diagnosed subjects.

Administration of the Disclosed Compositions in Subjects with End Stage Renal Disease (ESRD) to Reverse or Slow the Progression of Tissue Calcification:

This example describes the administration of the disclosed compositions to a subject with ESRD and on stable hemodialysis. The administration of the disclosed compositions will result in a change in aortic compliance (via plethysmography), vascular calcification and certain biomarker levels indicative of slowing the progression of, arresting, or reversing tissue calcification.

ESRD subjects on stable hemodialysis orally receive the disclosed compositions at 0.1 mg, 3 mg, 5 mg or 10 mg once daily for least 2 weeks, 4 weeks, 6 weeks, 8 weeks, 3 months, 6 months, 1 year, or indefinitely. The dosage form is a 0.1 mg, 3 mg, 5 mg or 10 mg tablet or soft-gel capsule. Two 25 mg capsules are administered once daily to the 50 mg dosage cohort.

A 50 y.o., 65 kg male patient diagnosed with the typical symptoms associated with moderate calciphylaxis is treated with 0.1 mg of the composition for a period of 8 weeks. After the treatment period, the patient is admitted and evaluated. The patient was found to have a significant change in the examined biomarker levels suggesting about a 10% reduction in vascular calcification and is also shown to have a 10% reduction in tissue calcification.

A 65 y.o., 45 kg female patient diagnosed with the typical symptoms associated with moderate calciphylaxis is treated with 0.1 mg of the composition for a period of 10 weeks. After the treatment period, the patient is admitted and evaluated. The patient was found to have a significant change in the examined biomarker levels suggesting about a 20% reduction in vascular calcification and is also shown to have a 15% reduction in tissue calcification.

A 55 y.o., 70 kg male patient diagnosed with the typical symptoms associated with moderate calciphylaxis is treated with 0.2 mg of the composition for a period of 3 months. After the treatment period, the patient is admitted and evaluated. The patient was found to have a significant change in the examined biomarker levels suggesting about a 25% reduction in vascular calcification and is also shown to have a 20% reduction in tissue calcification.

Coronary arterial calcium scores (CAC) are used to estimate the extent of calcification of thoracic arteries. A high CAC score is indicative of calcification, and treatment has the aim of arresting the long-term increase in CAC score, or reversing it, or slowing the rate of increase.

Aortic plethysmography also is used to measure arterial compliance, which decreases as calcification increases. Pulse wave velocity (PWV) also is measured to assess arterial compliance. The foregoing measures are useful in estimating the utility of treatments intended to prevent, slow the progression of, arrest or reverse vascular calcification. These measurements are used pre- and post-treatment with the disclosed compositions to assess treatment value.

Further, several biomarkers are assessed to determine the efficacy of the disclosed compositions at the three dose levels. Exemplary biomarkers include PIVKA-II; uncarboxylated and total Matrix Gla Protein (MGP); uncarboxylated, carboxylated and total osteocalcin protein; uncarboxylated, carboxylated and total Protein C, and hs-CRP. Blood samples are obtained to measure the biomarkers, most conveniently during patient visits for hemodialysis.

The administration of the disclosed compositions can result in (i) a decrease in PIVKA-II, which is indicative of slowing the progression of, arresting or reversing tissue calcification, (ii) a decrease in uncarboxylated MGP, uncarboxylated osteocalcin, and/or uncarboxylated Protein C, which is indicative of slowing the progression of, arresting or reversing tissue calcification, and/or (iii) a decrease in hs-CRP, which is indicative of slowing the progression of, arresting or reversing tissue calcification and/or reduced inflammation. Following the daily administration of 0.01 mg, 0.1 mg, 3 mg, 5 mg or 10 mg of the disclosed compositions, at least one of PIVKA-II, under-carboxylated Matrix Gla Protein (MGP), under-carboxylated osteocalcin protein, will show a change indicative of slowing the progression of, arresting or reversing tissue calcification.

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope.

The entire disclosures of all documents cited throughout this application are incorporated herein by reference.

What is claimed is:

1. A composition, comprising nanoparticles of MK-7 (menaquinone-7) or MKH2-7 (menaquinol-7), water and polyoxyl castor oil, wherein the nanoparticles have an average particle size of less than 125 nm.

2. The composition of claim 1, where the nanoparticles are prepared using a homogenizer selected from the group consisting of a rotor stator homogenizer, a bead mill homogenizer or a mortar and pestle homogenizer.

3. The composition of claim 1, further comprising at least one bioavailability enhancer selected from the group consisting of medium chain fatty acids, omega-3 fatty acids, capric acid, caprylic acid, alkylglycosides, chitosan, trimethylated chitosan, ethylene glycol tetraacetic acid, ethylene diamine tetraacetic acid, salicylic acid, genistein (5,7-Dihydroxy-3-(4-hydroxyphenyl)chromen-4-one)), and their pharmaceutically acceptable salts.

4. The composition of claim 1, wherein the composition is a nanosuspension in water.

5. The composition of claim 4, wherein the nanosuspension of MK-7 (menaquinone-7) or MKH2-7 (menaquinol-7) is at a concentration of 0.01 mg/mL in water.

6. The composition of claim 4, wherein the nanosuspension is in a water solution in a Fed State Simulated Intestinal Fluid (FeSSIF).

7. The composition of claim 1, further comprising a pharmaceutically acceptable excipient, wherein the composition is effective for the treatment of a condition associated with vitamin K.

8. The composition of claim 7, wherein the condition is osteoporosis or arteriosclerosis.

9. The composition of claim 1, wherein the nanoparticles have an average particle size of less than 115 nm, less than 100 nm, less than 90 nm, less than 80 nm or less than 75 nm.

10. The composition of claim 1, wherein the nanoparticles have an average particle size of less than 75 nm.

11. A method for the treatment of a disease in a mammal selected from the group consisting of neurodegenerative diseases, retinopathy, rheumatoid polyarthritis, atherosclerosis, amyotrophic lateral sclerosis, cerebral ischemia, cataracts, systemic infections, pathologies associated with cutaneous aging and with senescence in tissues, pathologies associated with mitochondrial dysfunction, cachexia associated with under nutrition, wherein the treatment is associated with the increase in the longevity of mammals, the method comprises the administration of a therapeutically effective amount of the composition of claim 1.

12. A method for treating a mammal with a disease selected from the group consisting of vitamin K deficiency, osteoporosis, a proliferative disease, and a cardiovascular disease, comprising administering to the mammal a therapeutically effective amount of the composition of claim 1.

13. A method for the treatment or prevention of osteoporosis and/or osteopenia, the method comprising administering to a patient in need of treatment, a therapeutically effective amount of a composition of claim 1.

14. A method of treating, preventing, slowing the progression of, arresting, and/or reversing calciphylaxis in a mammal in need thereof, the method comprising administering to the mammal a therapeutically effective amount of a composition of claim 1, and a pharmaceutically acceptable excipient, to prevent, slow the progression of, arrest, or reverse calciphylaxis.

15. The method of claim 14, wherein the mammal has distal calciphylaxis and/or central calciphylaxis.

16. The method of claim 14 or 15, wherein the mammal has diabetes, chronic kidney disease or end stage renal disease.

17. The method of claim 14, wherein the mammal has chronic obstructive pulmonary disease (COPD).

18. The method of claim 14, wherein the mammal has a calciphylaxis-related dermal lesion.

19. A method of treating, preventing, slowing the progression of, arresting and/or reversing tissue calcification in a pre-diabetic mammal (or subject) with diabetes, chronic kidney disease or a combination thereof, and in need thereof, the method comprising administering to the mammal at least 0.1 mg of the composition of any one of the composition of any one of claims 1 to 7 per day, to prevent, slow the progression of, and/or arrest tissue calcification, wherein the composition of claim 1 is administered in a pharmaceutical composition.

20. The method of claim 19, wherein the mammal has chronic kidney disease.

21. The method of claim 12, wherein the proliferative disease is selected from the group consisting of cancer, leukemia and an inflammatory disease.

22. A method for treating a mammal with a disease selected from the group consisting of vitamin K deficiency, osteoporosis, a proliferative disease, and a cardiovascular disease, comprising administering to the mammal a therapeutically effective amount of the composition of claim 1.

23. The method of claim 21, wherein the cancer is selected from the group consisting of melanoma, lung cancer, breast cancer, leukemia, neuroblastoma, glioblastoma, cervical, colorectal, pancreatic, bladder, renal, prostate, ovarian and head and neck.

24. A method for treating, preventing, slowing the progression of, arresting and/or reversing Alzheimer's disease (AD) in a mammal or a subject in need thereof, the method comprising administering to the mammal or subject at least 0.1 mg of the composition of any one of the composition of claim 1 per day, to prevent, slow the progression of, and/or arrest or reverse Alzheimer's disease.

* * * * *